US010087168B2

(12) United States Patent
Golden et al.

(10) Patent No.: US 10,087,168 B2
(45) Date of Patent: Oct. 2, 2018

(54) 6-SUBSTITUTED QUINAZOLINONE INHIBITORS

(71) Applicants: University of Kansas, Lawrence, KS (US); University of Louisville Research Foundation, Inc., Louisville, KS (US); Southern Research Institute, Birmingham, AL (US)

(72) Inventors: Jennifer Golden, Olathe, KS (US); Jeffrey Aube, Lawrence, KS (US); Donghoon Chung, Louisville, KY (US); Chad Schroeder, Lawrence, KS (US); Tuanli Yao, Lawrence, KS (US); E. Lucile White, Birmingham, AL (US); Nichole A. Tower, South Birmingham, AL (US)

(73) Assignees: UNIVERSITY OF KANSAS, Lawrence, KS (US); UNIVERSITY OF LOUISVILLE RESEARCH FOUNDATION, INC., Louisville, KY (US); SOUTHERN RESEARCH INSTITUTE, Birmingham, AL (US)

( * ) Notice: Subject to any disclaimer, the term of this patent is extended or adjusted under 35 U.S.C. 154(b) by 0 days.

(21) Appl. No.: 15/443,232

(22) Filed: Feb. 27, 2017

(65) Prior Publication Data

US 2017/0166557 A1 Jun. 15, 2017

Related U.S. Application Data

(62) Division of application No. 14/651,777, filed as application No. PCT/US2013/075092 on Dec. 13, 2013, now Pat. No. 9,580,393.

(Continued)

(51) Int. Cl.
*C07D 409/04* (2006.01)
*C07D 239/91* (2006.01)
(Continued)

(52) U.S. Cl.
CPC ......... *C07D 409/04* (2013.01); *C07D 239/90* (2013.01); *C07D 239/91* (2013.01);
(Continued)

(58) Field of Classification Search
CPC .................................................. C07D 409/04
See application file for complete search history.

(56) References Cited

U.S. PATENT DOCUMENTS 5,672,662 A 9/1997 Harris et al.
2004/0214783 A1 10/2004 Terman
(Continued)

FOREIGN PATENT DOCUMENTS

WO WO-2006/081331 8/2006
WO WO-2008/094909 8/2008
(Continued)

OTHER PUBLICATIONS

Tani et al., Studies on biologically active halogenated compounds. II. Chemical modifications of 6-amino-2-fluoromethyl-3-[o-tolyl]-4[3H]-quinazolinone and the CNS depressant activities of related compounds Chemical & Pharmaceutical Bulletin (1979), 27(11), 2675-87 CODEN: CPBTAL; ISSN: 0009-2363; English.*

*Primary Examiner* — Paul V Ward
(74) *Attorney, Agent, or Firm* — Foley & Lardner

(57) ABSTRACT

The present technology relates to compounds and compositions of Formulas I-III and methods using such compounds. The compounds and compositions described herein may be used in the treatment or prophylaxis of diseases associated with an alphavirus, for example, Venezuelan equine encephalitis virus (VEEV).

16 Claims, 1 Drawing Sheet

Related U.S. Application Data

(60) Provisional application No. 61/737,005, filed on Dec. 13, 2012, provisional application No. 61/853,740, filed on Apr. 11, 2013.

(51) Int. Cl.
| | |
|---|---|
| *C07D 403/12* | (2006.01) |
| *C07D 239/90* | (2006.01) |
| *C07D 403/06* | (2006.01) |
| *C07D 401/04* | (2006.01) |
| *C07D 239/95* | (2006.01) |

(52) U.S. Cl.
CPC ......... *C07D 239/95* (2013.01); *C07D 401/04* (2013.01); *C07D 403/06* (2013.01); *C07D 403/12* (2013.01)

(56) References Cited

U.S. PATENT DOCUMENTS

| | | |
|---|---|---|
| 2007/0066632 A1 | 3/2007 | Hart et al. |
| 2008/0188488 A1 | 8/2008 | Kamboj et al. |

FOREIGN PATENT DOCUMENTS

| | | | |
|---|---|---|---|
| WO | WO2008153701 | * | 12/2008 |
| WO | WO-2012/083112 | | 6/2012 |

\* cited by examiner

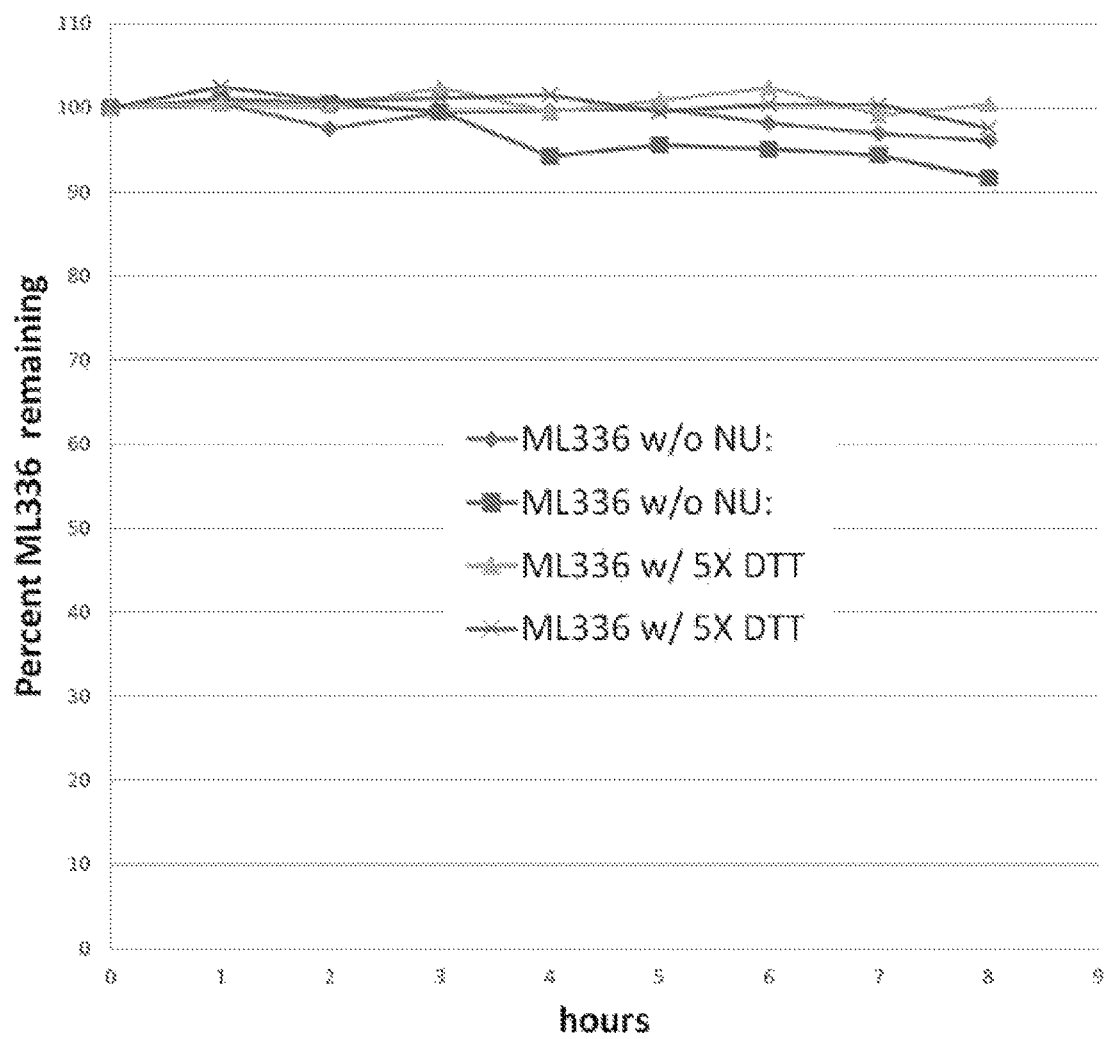

6-SUBSTITUTED QUINAZOLINONE INHIBITORS

CROSS-REFERENCE TO RELATED PATENT APPLICATIONS

This application is a divisional of U.S. patent application Ser. No. 14/651,777, now U.S. Pat. No. 9,580,393, filed Jun. 12, 2015, which is the U.S. 371 National Stage application of International Application No. PCT/US2013/075092, filed on Dec. 13, 2013, which claims priority to U.S. Provisional Patent Application No. 61/737,005, filed Dec. 13, 2012, and U.S. Provisional Patent Application No. 61/853,740, filed on Apr. 11, 2013, the entire disclosures of each of which are hereby incorporated by reference in their entireties for any and all purposes.

GOVERNMENT FUNDING

This invention was made with government support under U54 HG005031, R03 MH087448, and U54 HG005034 awarded by the National Institutes of Health. The government has certain rights in the invention.

FIELD

The present technology is directed to compounds, compositions, and methods to treat an alphavirus. The technology is especially suited to treat Venezuelan equine encephalitis virus (VEEV).

SUMMARY

The present technology is directed to compounds, compositions, and methods to treat an alphavirus. The technology is especially suited to treat encephalitis alphaviruses. The compounds and compositions described herein may be used in the treatment or prophylaxis of diseases that include, for example, infections by alphaviruses.

In one aspect of the present technology, a compound of Formula I, II, or III is provided:

stereoisomers thereof and pharmaceutically acceptable salts thereof, wherein W is CH or N; $X_1$ is an electron withdrawing group; $X_2$ is hydrogen or an electron withdrawing group; Y is O or S; $R_1$ is an alkyl group, an aryl group, an aralkyl group, or a heteroaryl group; $R_2$ is hydrogen or alkyl; $R_3$ is a hydrogen, alkyl, aryl, cycloalkyl, or non-aromatic heterocyclyl; $R_4$ is a hydrogen, alkyl, aryl, cycloalkyl, or non-aromatic heterocyclyl; $\alpha$ is 0 or 1; B is CH, C-alkyl, O, or N; with the provision that when B is O, $R_4$ is absent; Z is selected from the group consisting of where $R_5$ is a hydrogen, alkyl, aryl, cycloalkyl, or non-aromatic heterocyclyl; A is CH, C-alkyl, or N; and n is 1, 2, 3, or 4. In some embodiments, the electron withdrawing group is a halogen, a nitro group, cyano group, an alkanoyl group, a carbamoyl group, an ester, a sulfonyl group, a trialkyl ammonium group, or a trifluoromethyl group. In some embodiments, the electron withdrawing group is a halogen, a nitro group, a cyano group, or a trifluoromethyl group. In some embodiments, $X_2$ is hydrogen, a halogen, a nitro group, or a cyano group. In some embodiments, $X_2$ is hydrogen or a halogen. In some embodiments, $X_2$ is hydrogen. In some embodiments, $R_2$ is hydrogen.

In some embodiments, the compound is of Formulas I, II, or III and Y is O; $R_1$ is a heteroaryl group or a phenyl group, wherein the phenyl group is of Formula IA:

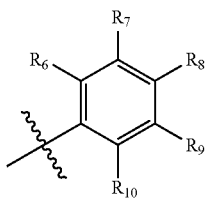

where $R_6R_7$, $R_8$, $R_9$ and $R_{10}$ are each independently hydrogen, halo, alkoxy, alkanoyl, carbamoyl, cyano, trifluoromethyl, or nitro; $R_2$ is hydrogen; $\alpha$ is 1; $R_3$ is a hydrogen or alkyl, $R_4$ and $R_5$ are each independently hydrogen, alkyl, aryl, cycloalkyl, non-aromatic heterocyclyl, alkanoyl, or carbamoyl; A is CH, C-alkyl or N; B is CH, C-alkyl, O, or N; with the provision that when B is O, $R_4$ is absent; and n is 1, 2, or 3.

In some embodiments, the compound is of Formulas I, II, or III and $X_2$ is hydrogen; Y is O; $R_1$ is an alkyl group, a heteroaryl group, or a phenyl group wherein the phenyl group is of Formula IA where $R_6$ is hydrogen, methoxy, halo, alkanoyl, or nitro; $R_7$ and $R_8$ are each independently hydrogen, alkoxy, aryloxy, halo, alkanoyl, or nitro; $R_9$ and $R_{10}$ are each independently hydrogen; $R_2$ is hydrogen; $\alpha$ is 1; Z is selected from the group consisting of

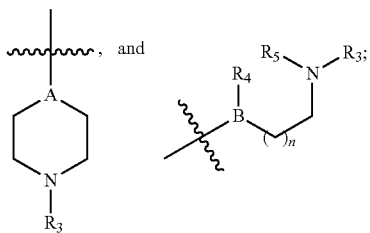

where $R_3$ is hydrogen or alkyl; $R_4$ and $R_5$ are each independently hydrogen, alkyl, aryl, cycloalkyl, non-aromatic heterocyclyl, or alkanoyl; A is CH, C-alkyl, or N; B is CH, C-alkyl, or N; and n is 2 or 3.

In some embodiments, the compound is of Formulas I, II, or III and $X_1$ is a halogen, a nitro group, or cyano group; $X_2$ is hydrogen; Y is O; $R_1$ is a methyl group, an ethyl group, or a phenyl group, wherein the phenyl group is of Formula IA where $R_6$, $R_7$, and $R_8$ are each independently hydrogen, methoxy, halo, or nitro; $R_9$ and $R_{10}$ are each independently hydrogen; $R_2$ is hydrogen; $\alpha$ is 1; Z is selected from the group consisting of

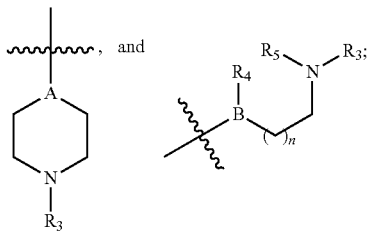

where $R_3$ is hydrogen or alkyl; $R_4$ and $R_5$ are each independently hydrogen, alkyl, cycloalkyl, or non-aromatic heterocyclyl; A is CH, C-alkyl, or N; B is CH, C-alkyl, or N; and n is 2 or 3.

In some embodiments, $R_6$ is hydrogen. In some embodiments, Z is

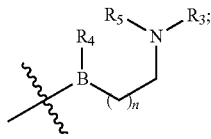

$R_3$ is methyl or ethyl, $R_4$ is methyl, and $R_5$ is hydrogen. In some embodiments, Z is

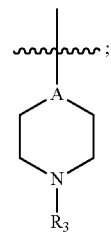

and $R_3$ is hydrogen. In some embodiments, W is CH. In some embodiments, $R_1$ is a phenyl group of Formula IA where $R_6$ is hydrogen; $R_7$, and $R_8$ are each independently hydrogen, methoxy, or halo; and $R_9$ and $R_{10}$ are each independently hydrogen.

In some embodiments, the compound is of Formula I.

In some embodiments, the compound is of Formulas II or III; $R_1$ is an alkyl group, an aralkyl group, a heteroaryl group, or a phenyl group, wherein the phenyl group is of Formula IA where $R_6R_7$, $R_8$, $R_9$ and $R_{10}$ are each independently hydrogen, halo, alkoxy, alkanoyl, carbamoyl, cyano, trifluoromethyl, or nitro. In some embodiments, the compound is of Formulas II or III, $R_1$ is an alkyl group, an aralkyl group, a heteroaryl group, or a phenyl group, wherein the phenyl group is of Formula IA where $R_6$, $R_7$, $R_9$, and $R_{10}$ are each independently hydrogen, halo, alkoxy, alkanoyl, carbamoyl, cyano, trifluoromethyl, or nitro; and $R_8$ is hydrogen, halo, substituted alkoxy, alkanoyl, carbamoyl, cyano, trifluoromethyl, or nitro.

In some embodiments, the compound is of Formulas II or III; $R_1$ is an alkyl group, an aralkyl group, a heteroaryl group, or a phenyl group, wherein the phenyl group is of Formula IA where $R_6$, $R_7$, $R_9$, and $R_{10}$ are each independently hydrogen, halo, alkoxy, alkanoyl, carbamoyl, cyano, trifluoromethyl, or nitro; and $R_8$ is hydrogen, halo, cycloalkoxy, alkanoyl, carbamoyl, cyano, trifluoromethyl, or nitro. In some embodiments, the compound is of Formulas II or III; $R_1$ is an alkyl group, an aralkyl group, a heteroaryl group, or a phenyl group, wherein the phenyl group is of Formula IA where $R_6$, $R_7$, $R_9$, and $R_{10}$ are each independently hydrogen, halo, alkoxy, alkanoyl, carbamoyl, cyano, trifluoromethyl, or nitro; and $R_8$ is hydrogen, halo, alkanoyl, carbamoyl, cyano, trifluoromethyl, or nitro.

In some embodiments, the compound is of Formulas II or III; $R_1$ is an alkyl group, an aralkyl group, a heteroaryl group, or a phenyl group, wherein the phenyl group is of Formula IA where $R_6R_7$, $R_8$, $R_9$ and $R_{10}$ are each independently hydrogen, halo, alkanoyl, carbamoyl, cyano, trifluoromethyl, or nitro.

In some embodiments, the compound is of Formulas II or III; $R_1$ is an alkyl group, an aralkyl group, a heteroaryl group, or a phenyl group wherein the phenyl group is of Formula IA where $R_6$ is hydrogen, methoxy, halo, alkanoyl, or nitro; $R_7$ and $R_8$ are each independently hydrogen, alkoxy, aryloxy, halo, alkanoyl, or nitro; and $R_9$ and $R_{10}$ are each independently hydrogen. In some embodiments, the compound is of Formulas II or III; Y is O; $R_1$ is a heteroaryl group or a phenyl group, wherein the phenyl group is of Formula IA where $R_6 R_7$, $R_8$, $R_9$ and $R_{10}$ are each independently hydrogen, halo, alkoxy, alkanoyl, carbamoyl, cyano, trifluoromethyl, or nitro; $R_2$ is hydrogen; α is 1; $R_4$ and $R_5$ are each independently hydrogen, alkyl, aryl, cycloalkyl, non-aromatic heterocyclyl, alkanoyl, or carbamoyl; and B is CH, C-alkyl, O, or N; with the provision that when B is O, $R_4$ is absent.

In some embodiments, the compound is of Formulas II or III; $X_2$ is hydrogen; Y is O; $R_1$ is an alkyl group, a substituted or unsubstituted benzyl group, a heteroaryl group, or a phenyl group wherein the phenyl group is of Formula IA where $R_6$ is hydrogen, methoxy, halo, alkanoyl, or nitro; $R_7$ and $R_8$ are each independently hydrogen, alkoxy, aryloxy, halo, alkanoyl, or nitro; $R_9$ and $R_{10}$ are each independently hydrogen; $R_2$ is hydrogen; α is 1; $R_4$ and $R_5$ are each independently hydrogen, alkyl, aryl, cycloalkyl, non-aromatic heterocyclyl, or alkanoyl; and B is CH, C-alkyl, or N.

In some embodiments, the compound is of Formulas II or III; $X_1$ is a halogen, a nitro group, a trifluoromethyl group, or a cyano group; $X_2$ is hydrogen; Y is O; $R_1$ is a methyl group, an ethyl group, a benzyl group, or a phenyl group, wherein the phenyl group is of Formula IA where $R_6$, $R_7$, and $R_8$ are each independently hydrogen, methoxy, halo, or nitro; $R_9$ and $R_{10}$ are each independently hydrogen; $R_2$ is hydrogen; α is 1; $R_4$ and $R_5$ are each independently hydrogen, alkyl, cycloalkyl, or non-aromatic heterocyclyl; B is CH, C-alkyl, or N.

In some embodiments, $R_6$ is hydrogen. In some embodiments, $R_3$ is methyl or ethyl; and $R_4$ is methyl. In some embodiments W is CH. In some embodiments, $R_1$ is a phenyl group of Formula IA where $R_6$ is hydrogen; $R_7$, and $R_8$ are each independently hydrogen, methoxy, or halo; $R_9$ and $R_{10}$ are each independently hydrogen. In some embodiments, the compound is of Formula II. In some embodiments, the compound is of Formula III.

In some embodiments, the compound is:
2-((4-ethylpiperazin-1-yl)methyl)-6-nitro-3-phenylquinazolin-4(3H)-one,
6-nitro-3-phenyl-2-(piperazin-1-ylmethyl)quinazolin-4(3H)-one,
6-nitro-2-(piperazin-1-ylmethyl)-3-(thiophen-3-yl)quinazolin-4(3H)-one,
3-(2-fluorophenyl)-2-((4-methylpiperazin-1-yl)methyl)-6-nitroquinazolin-4(3H)-one,
2-((4-ethylpiperazin-1-yl)methyl)-3-(2-fluorophenyl)-6-nitroquinazolin-4(3H)-one,
2-((4-ethylpiperazin-1-yl)methyl)-3-(3-fluorophenyl)-6-nitroquinazolin-4(3H)-one, 2-((4-ethylpiperazin-1-yl)methyl)-3-(4-fluorophenyl)-6-nitroquinazolin-4(3H)-one,
3-(2-fluorophenyl)-2-((4-isopropylpiperazin-1-yl)methyl)-6-nitroquinazolin-4(3H)-one,
3-(2-fluorophenyl)-6-nitro-2-(piperazin-1-ylmethyl)quinazolin-4(3H)-one,
3-(2-fluorophenyl)-2-(morpholinomethyl)-6-nitroquinazolin-4(3H)-one,
3-(2-fluorophenyl)-6-nitro-2-(piperidin-1-ylmethyl)quinazolin-4(3H)-one,
3-(3-methoxyphenyl)-6-nitro-2-(piperazin-1-ylmethyl)quinazolin-4(3H)-one,
3-(4-methoxyphenyl)-6-nitro-2-(piperazin-1-ylmethyl)quinazolin-4(3H)-one,
2-((4-ethylpiperazin-1-yl)methyl)-6-iodo-3-phenylquinazolin-4(3H)-one,
2-((4-ethylpiperazin-1-yl)methyl)-4-oxo-3-phenyl-3,4-dihydroquinazoline-6-carbonitrile,
6-nitro-3-phenyl-2-((tetrahydropyrimidin-1(2H)-yl)methyl)quinazolin-4(3H)-one,
2((1,4-diazepan-1-yl)methyl)-6-nitro-3-phenylquinazolin4(3H)-one,
2-((methyl(2-(methylamino)ethyl)amino)methyl)-6-nitro-3-phenylquinazolin-4(3H)-one,
2-((methyl(3-(methylamino)propyl)amino)methyl)-6-nitro-3-phenylquinazolin-4(3H)-one,
2-(((2-(ethylamino)ethyl)(methyl)amino)methyl)-6-nitro-3-phenylquinazolin-4(3H)-one,
3-(4-methoxyphenyl)-2-((methyl(2-(methylamino)ethyl)amino)methyl)-6-nitroquinazolin-4(3H)-one,
3-(2-fluorophenyl)-2-((methyl(2-(methylamino)ethyl)amino)methyl)-6-nitroquinazolin-4(3H)-one,
3-(3-fluorophenyl)-2-((methyl(2-(methylamino)ethyl)amino)methyl)-4-oxo-3,4-dihydroquinazoline-6-carbonitrile,
6-fluoro-2-((methyl(2-(methylamino)ethyl)amino)methyl)-3-phenylquinazolin-4(3H)-one,
2-((methyl(2-(methylamino)ethyl)amino)methyl)-4-oxo-3-phenyl-3,4-dihydroquinazoline-6-carbonitrile,
2-((4-ethylpiperazin-1-yl)methyl)-6-nitro-3-phenylpyrido[2,3-d]pyrimidin-4(3H)-one,
6-nitro-3-phenyl-2-(piperidin-4-yl)quinazolin-4(3H)-one,
(E)-2-((1,4-dimethylpiperazin-2-ylidene)amino)-5-nitro-N-phenylbenzamide,
(E)-5-cyano-2-((1,4-dimethylpiperazin-2-ylidene)amino)-N-phenylbenzamide,
(E)-2-((1,4-dimethylpiperazin-2-ylidene)amino)-N-(4-methoxyphenyl)-5-nitrobenzamide,
(E)-2-((1,4-dimethylpiperazin-2-ylidene)amino)-N-(2-fluorophenyl)-5-nitrobenzamide,
(E)-4-chloro-5-cyano-2-((1,4-dimethylpiperazin-2-ylidene)amino)-N-phenylbenzamide,
(E)-2-((1-ethyl-4-methylpiperazin-2-ylidene)amino)-5-nitro-N-phenylbenzamide,
(E)-2-((1,4-dimethylpiperazin-2-ylidene)amino)-5-fluoro-N-phenylbenzamide,
(E)-5-cyano-2-((1,4-dimethylpiperazin-2-ylidene)amino)-N-(2-fluorophenyl)benzamide,
(E)-5-cyano-2-((1,4-dimethylpiperazin-2-ylidene)amino)-N-(3-fluorophenyl)benzamide,
(E)-2-((1,4-dimethylpiperazin-2-ylidene)amino)-N-(4-methoxyphenyl)-5-nitrobenzamide,
(E)-2-((1,4-dimethylpiperazin-2-ylidene)amino)-N-(3-fluorophenyl)-5-nitrobenzamide,
(E)-2-((1,4-dimethylpiperazin-2-ylidene)amino)-N-phenyl-5-(trifluoromethyl)benzamide,
(E)-2-((1,4-dimethylpiperazin-2-ylidene)amino)-N-(4-fluorophenyl)-5-nitrobenzamide,
(E)-2-((1,4-dimethylpiperazin-2-ylidene)amino)-N-(2-methoxyphenyl)-5-nitrobenzamide,
(E)-2-((1,4-dimethylpiperazin-2-ylidene)amino)-N-(3-methoxyphenyl)-5-nitrobenzamide,
(E)-2-((1,4-dimethylpiperazin-2-ylidene)amino)-N-isopropyl-5-nitrobenzamide,
(E)-N-benzyl-2-((1,4-dimethylpiperazin-2-ylidene)amino)-5-nitrobenzamide,
(E)-4-((1,4-dimethylpiperazin-2-ylidene)amino)-N-phenylpyridazine-3-carboxamide,
(E)-methyl 4-((1,4-dimethylpiperazin-2-ylidene)amino)-3-(phenylcarbamoyl)benzoate, (E)-2-((1,4-dimethylpiperazin-2-ylidene)amino)-5-nitro-N-(thiophen-3-yl)benzamide,
(E)-2-((1,4-dimethylpiperazin-2-ylidene)amino)-4,5-difluoro-N-phenylbenzamide,
(E)-5-cyano-2-((1,4-dimethylpiperazin-2-ylidene)amino)-4-fluoro-N-phenylbenzamide,
(E)-2-((1,4-dimethylpiperazin-2-ylidene)amino)-N-methyl-5-nitrobenzamide,
(Z)-2-((1,4-dimethylpiperazin-2-ylidene)amino)-5-nitro-N-phenylbenzamide,
(Z)-5-cyano-2-((1,4-dimethylpiperazin-2-ylidene)amino)-N-phenylbenzamide,
(Z)-2-((1,4-dimethylpiperazin-2-ylidene)amino)-N-(4-methoxyphenyl)-5-nitrobenzamide,
(Z)-2-((1,4-dimethylpiperazin-2-ylidene)amino)-N-(2-fluorophenyl)-5-nitrobenzamide,
(Z)-4-chloro-5-cyano-2-((1,4-dimethylpiperazin-2-ylidene)amino)-N-phenylbenzamide,
(Z)-2-((1-ethyl-4-methylpiperazin-2-ylidene)amino)-5-nitro-N-phenylbenzamide,
(Z)-2-((1,4-dimethylpiperazin-2-ylidene)amino)-5-fluoro-N-phenylbenzamide,
(Z)-5-cyano-2-((1,4-dimethylpiperazin-2-ylidene)amino)-N-(2-fluorophenyl)benzamide,
(Z)-5-cyano-2-((1,4-dimethylpiperazin-2-ylidene)amino)-N-(3-fluorophenyl)benzamide,
(Z)-2-((1,4-dimethylpiperazin-2-ylidene)amino)-N-(4-methoxyphenyl)-5-nitrobenzamide,
(Z)-2-((1,4-dimethylpiperazin-2-ylidene)amino)-N-(3-fluorophenyl)-5-nitrobenzamide,
(Z)-2-((1,4-dimethylpiperazin-2-ylidene)amino)-N-phenyl-5-(trifluoromethyl)benzamide,
(Z)-2-((1,4-dimethylpiperazin-2-ylidene)amino)-N-(4-fluorophenyl)-5-nitrobenzamide,
(Z)-2-((1,4-dimethylpiperazin-2-ylidene)amino)-N-(2-methoxyphenyl)-5-nitrobenzamide,
(Z)-2-((1,4-dimethylpiperazin-2-ylidene)amino)-N-(3-methoxyphenyl)-5-nitrobenzamide,
(Z)-2-((1,4-dimethylpiperazin-2-ylidene)amino)-N-isopropyl-5-nitrobenzamide,
(Z)—N-benzyl-2-((1,4-dimethylpiperazin-2-ylidene)amino)-5-nitrobenzamide,
(Z)-4-((1,4-dimethylpiperazin-2-ylidene)amino)-N-phenylpyridazine-3-carboxamide,
(Z)-methyl 4-((1,4-dimethylpiperazin-2-ylidene)amino)-3-(phenylcarbamoyl)benzoate,
(Z)-2-((1,4-dimethylpiperazin-2-ylidene)amino)-5-nitro-N-(thiophen-3-yl)benzamide,
(Z)-2-((1,4-dimethylpiperazin-2-ylidene)amino)-4,5-difluoro-N-phenylbenzamide,
(Z)-5-cyano-2-((1,4-dimethylpiperazin-2-ylidene)amino)-4-fluoro-N-phenylbenzamide, or
(Z)-2-((1,4-dimethylpiperazin-2-ylidene)amino)-N-methyl-5-nitrobenzamide.

In some embodiments, the compound is
(E)-2-((1,4-dimethylpiperazin-2-ylidene)amino)-5-nitro-N-phenylbenzamide,
(E)-5-cyano-2-((1,4-dimethylpiperazin-2-ylidene)amino)-N-phenylbenzamide,
(E)-2-((1,4-dimethylpiperazin-2-ylidene)amino)-N-(4-methoxyphenyl)-5-nitrobenzamide,
(E)-2-((1,4-dimethylpiperazin-2-ylidene)amino)-N-(2-fluorophenyl)-5-nitrobenzamide,
(E)-4-chloro-5-cyano-2-((1,4-dimethylpiperazin-2-ylidene)amino)-N-phenylbenzamide,
(E)-2-((1-ethyl-4-methylpiperazin-2-ylidene)amino)-5-nitro-N-phenylbenzamide,
(E)-2-(1,4-dimethylpiperazin-2-ylidene)amino)-5-fluoro-N-phenylbenzamide,
(E)-5-cyano-2-((1,4-dimethylpiperazin-2-ylidene)amino)-N-(2-fluorophenyl)benzamide,
(E)-5-cyano-2-((1,4-dimethylpiperazin-2-ylidene)amino)-N-(3-fluorophenyl)benzamide,
(E)-2-((1,4-dimethylpiperazin-2-ylidene)amino)-N-(4-methoxyphenyl)-5-nitrobenzamide,
(E)-2-((1,4-dimethylpiperazin-2-ylidene)amino)-N-(3-fluorophenyl)-5-nitrobenzamide,
(E)-2-((1,4-dimethylpiperazin-2-ylidene)amino)-N-phenyl-5-(trifluoromethyl)benzamide,
(E)-2-((1,4-dimethylpiperazin-2-ylidene)amino)-N-(4-fluorophenyl)-5-nitrobenzamide,
(E)-2-((1,4-dimethylpiperazin-2-ylidene)amino)-N-(2-methoxyphenyl)-5-nitrobenzamide,
(E)-2-((1,4-dimethylpiperazin-2-ylidene)amino)-N-(3-methoxyphenyl)-5-nitrobenzamide,
(E)-2-((1,4-dimethylpiperazin-2-ylidene)amino)-N-isopropyl-5-nitrobenzamide,
(E)-N-benzyl-2-((1,4-dimethylpiperazin-2-ylidene)amino)-5-nitrobenzamide,
(E)-4-((1,4-dimethylpiperazin-2-ylidene)amino)-N-phenylpyridazine-3-carboxamide,
(E)-methyl 4-((1,4-dimethylpiperazin-2-ylidene)amino)-3-(phenylcarbamoyl)benzoate,
(E)-2-((1,4-dimethylpiperazin-2-ylidene)amino)-5-nitro-N-(thiophen-3-yl)benzamide,
(E)-2-((1,4-dimethylpiperazin-2-ylidene)amino)-4,5-difluoro-N-phenylbenzamide,
(E)-5-cyano-2-((1,4-dimethylpiperazin-2-ylidene)amino)-4-fluoro-N-phenylbenzamide, or
(E)-2-((1,4-dimethylpiperazin-2-ylidene)amino)-N-methyl-5-nitrobenzamide.

In some embodiments, the compound is
2-((4-ethylpiperazin-1-yl)methyl)-6-nitro-3-phenylquinazolin-4(3H)-one,
6-nitro-3-phenyl-2-(piperazin-1-ylmethyl)quinazolin-4(3H)-one,
6-nitro-2-(piperazin-1-ylmethyl)-3-(thiophen-3-yl)quinazolin-4(3H)-one,
3-(2-fluorophenyl)-2-((4-methylpiperazin-1-yl)methyl)-6-nitroquinazolin-4(3H)-one,
2-((4-ethylpiperazin-1-yl)methyl)-3-(2-fluorophenyl)-6-nitroquinazolin-4(3H)-one,
2-((4-ethylpiperazin-1-yl)methyl)-3-(3-fluorophenyl)-6-nitroquinazolin-4(3H)-one, 2-((4-ethylpiperazin-1-yl)methyl)-3-(4-fluorophenyl)-6-nitroquinazolin-4(3H)-one,
3-(2-fluorophenyl)-2-((4-isopropylpiperazin-1-yl)methyl)-6-nitroquinazolin-4(3H)-one,
3-(2-fluorophenyl)-6-nitro-2-(piperazin-1-ylmethyl)quinazolin-4(3H)-one,
3-(2-fluorophenyl)-2-(morpholinomethyl)-6-nitroquinazolin-4(3H)-one,
3-(2-fluorophenyl)-6-nitro-2-(piperidin-1-ylmethyl)quinazolin-4(3H)-one,
3-(3-methoxyphenyl)-6-nitro-2-(piperazin-1-ylmethyl)quinazolin-4(3H)-one,
3-(4-methoxyphenyl)-6-nitro-2-(piperazin-1-ylmethyl)quinazolin-4(3H)-one,
2-((4-ethylpiperazin-1-yl)methyl)-6-iodo-3-phenylquinazolin-4(3H)-one,
2-((4-ethylpiperazin-1-yl)methyl)-4-oxo-3-phenyl-3,4-dihydroquinazoline-6-carbonitrile,
6-nitro-3-phenyl-2-((tetrahydropyrimidin-1(2H)-yl)methyl)quinazolin-4(3H)-one, 2-((1,4-diazepan-1-yl)methyl)-6-nitro-3-phenylquinazolin-4(3H)-one,
2-((methyl(2-(methylamino)ethyl)amino)methyl)-6-nitro-3-phenylquinazolin-4(3H)-one,
2-((methyl(3-(methylamino)propyl)amino)methyl)-6-nitro-3-phenylquinazolin-4(3H)-one,
2-(((2-(ethylamino)ethyl)(methyl)amino)methyl)-6-nitro-3-phenylquinazolin-4(3H)-one,
3-(4-methoxyphenyl)-2-((methyl(2-(methylamino)ethyl)amino)methyl)-6-nitroquinazolin-4(3H)-one,
3-(2-fluorophenyl)-2-((methyl(2-(methylamino)ethyl)amino)methyl)-6-nitroquinazolin-4(3H)-one,
3-(3-fluorophenyl)-2-((methyl(2-(methylamino)ethyl)amino)methyl)-4-oxo-3,4-dihydroquinazoline-6-carbonitrile,
6-fluoro-2-((methyl(2-(methylamino)ethyl)amino)methyl)-3-phenylquinazolin-4(3H)-one,
2-((methyl(2-(methylamino)ethyl)amino)methyl)-4-oxo-3-phenyl-3,4-dihydroquinazoline-6-carbonitrile,
2-((4-ethylpiperazin-1-yl)methyl)-6-nitro-3-phenylpyrido[2,3-d]pyrimidin-4(3H)-one, or
6-nitro-3-phenyl-2-(piperidin-4-yl)quinazolin-4(3H)-one.

In some embodiments, the compound is:
(Z)-2-((1,4-dimethylpiperazin-2-ylidene)amino)-5-nitro-N-phenylbenzamide,
(Z)-5-cyano-2-((1,4-dimethylpiperazin-2-ylidene)amino)-N-phenylbenzamide,
(Z)-2-((1,4-dimethylpiperazin-2-ylidene)amino)-N-(4-methoxyphenyl)-5-nitrobenzamide,
(Z)-2-((1,4-dimethylpiperazin-2-ylidene)amino)-N-(2-fluorophenyl)-5-nitrobenzamide,
(Z)-4-chloro-5-cyano-2-((1,4-dimethylpiperazin-2-ylidene)amino)-N-phenylbenzamide,
(Z)-2-((1-ethyl-4-methylpiperazin-2-ylidene)amino)-5-nitro-N-phenylbenzamide,
(Z)-2-((1,4-dimethylpiperazin-2-ylidene)amino)-5-fluoro-N-phenylbenzamide,
(Z)-5-cyano-2-((1,4-dimethylpiperazin-2-ylidene)amino)-N-(2-fluorophenyl)benzamide,
(Z)-5-cyano-2-((1,4-dimethylpiperazin-2-ylidene)amino)-N-(3-fluorophenyl)benzamide,
(Z)-2-((1,4-dimethylpiperazin-2-ylidene)amino)-N-(4-methoxyphenyl)-5-nitrobenzamide,
(Z)-2-((1,4-dimethylpiperazin-2-ylidene)amino)-N-(3-fluorophenyl)-5-nitrobenzamide,
(Z)-2-((1,4-dimethylpiperazin-2-ylidene)amino)-N-phenyl-5-(trifluoromethyl)benzamide,
(Z)-2-((1,4-dimethylpiperazin-2-ylidene)amino)-N-(4-fluorophenyl)-5-nitrobenzamide,
(Z)-2-((1,4-dimethylpiperazin-2-ylidene)amino)-N-(2-methoxyphenyl)-5-nitrobenzamide,
(Z)-2-((1,4-dimethylpiperazin-2-ylidene)amino)-N-(3-methoxyphenyl)-5-nitrobenzamide,
(Z)-2-((1,4-dimethylpiperazin-2-ylidene)amino)-N-isopropyl-5-nitrobenzamide,
(Z)—N-benzyl-2-((1,4-dimethylpiperazin-2-ylidene)amino)-5-nitrobenzamide,
(Z)-4-((1,4-dimethylpiperazin-2-ylidene)amino)-N-phenylpyridazine-3-carboxamide,
(Z)-methyl 4-((1,4-dimethylpiperazin-2-ylidene)amino)-3-(phenylcarbamoyl)benzoate,
(Z)-2-((1,4-dimethylpiperazin-2-ylidene)amino)-5-nitro-N-(thiophen-3-yl)benzamide,
(Z)-2-((1,4-dimethylpiperazin-2-ylidene)amino)-4,5-difluoro-N-phenylbenzamide,
(Z)-5-cyano-2-((1,4-dimethylpiperazin-2-ylidene)amino)-4-fluoro-N-phenylbenzamide, or
(Z)-2-((1,4-dimethylpiperazin-2-ylidene)amino)-N-methyl-5-nitrobenzamide.

In another aspect, the present technology provides a method comprising administering to a subject in need thereof an antiviral effective amount of a compound of Formulas I, II, or III. In the method, risk of infection by and/or transmission of an alphavirus by said subject is decreased.

In another aspect, a composition is provided including a compound of Formulas I, II, or III and a pharmaceutically acceptable carrier. In a related aspect, a pharmaceutical composition is provided for treating a viral infection, where the composition includes an effective amount of the compound of Formulas I, II, or III. In some embodiments, the viral infection comprises an alphavirus. In some embodiments, the viral infection comprises an encephalitic alphavirus. In some embodiments, the viral infection comprises a Venezuelan equine encephalitis virus. In some embodiments, the effective compound selectively treats the viral infection. Thus, the instant present technology provides pharmaceutical compositions and medicaments comprising any of the compounds disclosed herein (e.g., compounds of Formulas I, II, or III) and a pharmaceutically acceptable carrier or one or more excipients or fillers. The compositions may be used in the methods and treatments described herein. Such compositions include a viral inhibitory effective amount of any compound as described herein, including but not limited to a compound of Formulas I, II, or III. In some embodiments, the pharmaceutical composition is packaged in unit dosage form. The unit dosage form is effective in preventing infection by, reducing symptoms associated with, and/or reducing risk of transmission of an encephalitic alphavirus when administered to a subject in need thereof.

In one aspect, a method is provided for administering to a subject in need thereof an antiviral effective amount of a compound of the present technology. A subject in need thereof may be a patient suffering from or believed to be at risk of suffering from a disease associated with a virus, such as an encephalitic alphavirus. In some embodiments, the compound is effective in the treatment of an alphavirus. In some embodiments, the compound is effective in the treatment of an encephalitic alphavirus. In some embodiments, the compound is effective in the treatment of a Venezuelan equine encephalitis virus. In some embodiments, the compound selectively treats the viral infection. In some embodiments, the risk of infection by and/or transmission of an alphavirus by said subject is decreased. In any of these embodiments, the administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration.

DESCRIPTION OF THE DRAWINGS

FIG. 1 shows the chemical stability of ML336 over 8 h in the presence of a 5-fold concentration of dithiothreitol ("DTT"), according to one embodiment.

DETAILED DESCRIPTION

In various aspects, the present technology provides novel compounds and methods for treating a viral infection. The compounds provided herein can be formulated into pharmaceutical compositions and medicaments that are useful in the disclosed methods. Also provided is the use of the compounds in preparing pharmaceutical formulations and medicaments, the use of the compounds in treating a viral infection.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —CCH, —CCCH$_3$, —CH$_2$CCCH$_3$, —CCCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3] dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{31}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently a substituted or unsubstituted alkyl, alkenyl, alkynyl, cycloalkyl, aryl, aralkyl, heterocyclylalkyl, or heterocyclyl group as defined herein. R$^{33}$ may also be H.

The term "amine" (or "amino") as used herein refers to —NR$^{35}$R$^{36}$ groups, wherein R$^{35}$ and R$^{36}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{40}$ groups, sulfoxides include —S(O)R$^{41}$ groups, sulfones include —SO$_2$R$^{42}$ groups, and sulfonyls include —SO$_2$OR$^{43}$. R$^{40}$, R$^{41}$, R$^{42}$, and R$^{43}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{44}$—C(O)—NR$^{45}$R$^{46}$ groups. R$^{44}$, R$^{45}$, and R$^{46}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{47}$)NR$^{48}$R$^{49}$ and —NR$^{47}$C(NR$^{48}$)R$^{49}$, wherein R$^{47}$, R$^{48}$, and R$^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{50}$C(NR$^{51}$)NR$^{52}$R$^{53}$, wherein R$^{50}$, R$^{51}$, R$^{52}$ and R$^{53}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{54}$)=C(R$^{55}$)NR$^{56}$R$^{57}$ and —NR$^{54}$C(R$^{55}$)=C(R$^{56}$)R$^{57}$, wherein R$^{54}$, R$^{55}$, R$^{56}$ and R$^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxy' as used herein can refer to —OH or its ionized form, —O⁻.

The term "imide" refers to —C(O)NR$^{58}$C(O)R$^{59}$, wherein R$^{58}$ and R$^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{60}$(NR$^{61}$) and —N(CR$^{60}$R$^{61}$) groups, wherein R$^{60}$ and R$^{61}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{60}$ and R$^{61}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The phrase "selectively treats" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through a viral-specific mechanism of action, resulting in fewer off-target effects because the compounds target the virus and not the host. The phrase may further be modified as discussed herein, including Tables 2-9.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

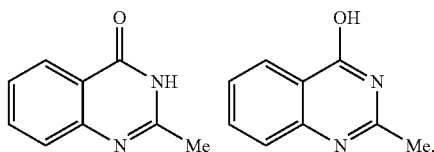

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

VEEV, a member of family Togaviridae, has been known to cause severe neurological diseases in humans and horses.

Epidemics have occurred affecting hundreds of thousands of people in the Americas for nearly a century. An estimated 70,000 to 100,000 humans and similar numbers of horses infected with VEEV were reported during the last outbreak in 1995. The disease in humans is characterized by fever, headache, and encephalitis to varying degrees and is sometimes fatal. The mortality rate is below 1%; however, the neurological disease is present in up to 14% of patients. The virus is usually transmitted via mosquito bite, but evidence supports viral transmission by aerosol. The modes of transmission make VEEV infection very difficult to control during outbreaks. Thus, prophylaxis and efficacious treatments are critical to minimizing the impact of the transmissible disease on human and equines.

Currently, there are no FDA-approved vaccines or therapeutics for the encephalitic alphaviruses, which limit treatment to supportive care. The US Army has been developing vaccines for VEEV as they appreciate the impact of the disease on soldiers as well as its potential use as a bioweapon. The vaccines, which are comprised of attenuated live virus, are still in the investigational new drug (IND) stage and are only available through the Special Immunization Program at United State Army Medical Research Institute of Infectious Diseases (USAMRIID) for protecting personnel working with the virus. A few other vaccine candidates are in the IND stage, such as formalized killed TC-83 vaccine and the live attenuated V3526 vaccine. Again those vaccines have not been FDA-approved due to lack of efficacy and adverse effects seen during clinical trials.

The alphaviruses, of which VEEV is a member, include other medically important viruses such as Eastern and Western equine encephalitis viruses (EEEV and WEEV respectively), Sindbis virus (SINV) and Chikungunya (CHIK) viruses. VEE, EEE and CHIK viruses are listed as Center for Disease Control (CDC) category B and C agents because of their potential military and bioterrorism threats. They are relatively easy to produce at high titers, are highly infectious by aerosol, and can cause severely debilitating disease and death. Finally, VEEV, eastern (EEEV), western (WEEV) and Chikungunya (CHIK) viruses are closely related phylogenetically. Therefore, discovery of VEEV inhibitors would be equally effective against closely related other encephalitic alphaviruses.

The present technology is directed to compounds, compositions, and methods to treat an alphavirus. The technology is especially suited to treat an encephalitic alphavirus. The compounds and compositions described herein may be used in the treatment or prophylaxis of diseases that include, for example, Venezuelan equine encephalitis virus (VEEV). Methods of treatment include administering to a subject in need thereof a therapeutically effective amount of a compound or composition described herein. The compounds of the present technology can also be used in the treatment or prophylaxis of a disease state or malady characterized by or associated with an alphavirus. Generally, prophylactic or prophylaxis relates to a reduction in the likelihood of the patient developing a disorder such as VEEV infection or proceeding to a diagnosis state for the disorder. For example, the compounds of the present technology can be used prophylacticly as a measure designed to preserve health and prevent the spread or maturation of disease in a patient. It is also appreciated that the various modes of treatment or prevention of a disease such as an alphavirus infection can mean "substantial" treatment or prevention, which includes total but also less than total treatment or prevention, and in which some biologically or medically relevant result is achieved. Furthermore, treatment or treating as well as alleviating can refer to therapeutic treatment and prophylactic or preventative measures in which the object is to prevent, slow down (lessen) a disease state, condition or malady. For example, a subject can be successfully treated for an alphavirus infection if, after receiving through administration an effective or therapeutic amount of one or more compounds described herein, the subject shows observable and/or measurable reduction in or absence of one or more signs and symptoms of the particular disease. The present technology also provides for methods of administering one or more compounds of the present technology to a patient in an effective amount for the treatment or prophylaxis of a disease such as, for example, an alphavirus infection.

While not wishing to be bound by theory, it is believed that the compounds and compositions disclosed herein act through a post-entry, viral-specific, mechanism of action by inhibiting viral replication through the nsP2 helicase, resulting in the prevention or treatment of diseases related to an encephalitic alphavirus. "Virus specific" means the compounds do not use host cellular machinery to inhibit virus. Thus, there are fewer off-target effects because the compounds target the virus and not host.

In one aspect of the present technology, a compound of Formula I, II, or III is provided:

stereoisomers thereof and pharmaceutically acceptable salts thereof, wherein W is CH or N; $X_1$ is an electron withdrawing group; $X_2$ is hydrogen or an electron withdrawing group; Y is O or S; $R_1$ is an alkyl group, an aryl group, an aralkyl group, or a heteroaryl group; $R_2$ is hydrogen or alkyl; $R_3$ is a hydrogen, alkyl, aryl, cycloalkyl, or non-aromatic heterocyclyl; $R_4$ is a hydrogen, alkyl, aryl, cycloalkyl, or non-aromatic heterocyclyl; α is 0 or 1; B is CH, C-alkyl, O, or N; with the provision that when B is O, $R_4$ is absent; Z is selected from the group consisting of

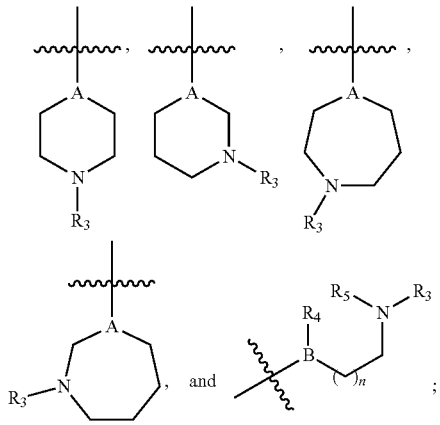

where $R_5$ is a hydrogen, alkyl, aryl, cycloalkyl, or non-aromatic heterocyclyl; A is CH, C-alkyl, or N; and n is 1, 2, 3, or 4. If both $X_1$ and $X_2$ are an electron withdrawing group, $X_1$ and $X_2$ may be different electron withdrawing groups or $X_1$ and $X_2$ may each independently bear the same electron withdrawing group. In some embodiments, the electron withdrawing group is a halogen, a nitro group, cyano group, an alkanoyl group, a carbamoyl group, an ester, a sulfonyl group, a trialkyl ammonium group, or a trifluoromethyl group. In some embodiments, the electron withdrawing group is a halogen, a nitro group, a cyano group, or a trifluoromethyl group. In some embodiments, $X_2$ is hydrogen, a halogen, a nitro group, or a cyano group. In some embodiments, $X_2$ is hydrogen or a halogen. In some embodiments, $X_2$ is hydrogen. In some embodiments, $R_2$ is hydrogen.

In some embodiments, the compound is of Formulas I, II, or III and Y is O; $R_1$ is a heteroaryl group or a phenyl group, wherein the phenyl group is of Formula IA:

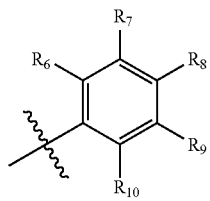

where $R_6$, $R_7$, $R_8$, $R_9$ and $R_{10}$ are each independently hydrogen, halo, alkoxy, alkanoyl, carbamoyl, cyano, trifluoromethyl, or nitro; $R_2$ is hydrogen; α is 1; $R_3$ is a hydrogen or alkyl, $R_4$ and $R_5$ are each independently hydrogen, alkyl, aryl, cycloalkyl, non-aromatic heterocyclyl, alkanoyl, or carbamoyl; A is CH, C-alkyl or N; B is CH, C-alkyl, O, or N; with the provision that when B is O, $R_4$ is absent; and n is 1, 2, or 3.

In some embodiments, the compound is of Formulas I, II, or III and $X_2$ is hydrogen; Y is O; $R_1$ is an alkyl group, a heteroaryl group, or a phenyl group wherein the phenyl group is of Formula IA where $R_6$ is hydrogen, methoxy, halo, alkanoyl, or nitro; $R_7$ and $R_8$ are each independently hydrogen, alkoxy, aryloxy, halo, alkanoyl, or nitro; $R_9$ and $R_{10}$ are each independently hydrogen; $R_2$ is hydrogen; α is 1; Z is selected from the group consisting of

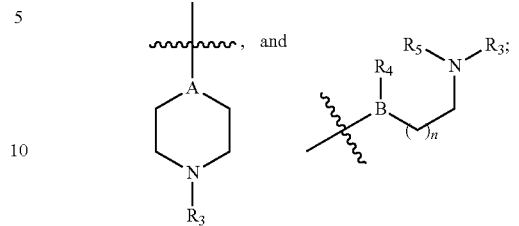

where $R_3$ is hydrogen or alkyl; $R_4$ and $R_5$ are each independently hydrogen, alkyl, aryl, cycloalkyl, non-aromatic heterocyclyl, or alkanoyl; A is CH, C-alkyl, or N; B is CH, C-alkyl, or N; and n is 2 or 3.

In some embodiments, the compound is of Formulas I, II, or III and $X_1$ is a halogen, a nitro group, or cyano group; $X_2$ is hydrogen; Y is O; $R_1$ is a methyl group, an ethyl group, or a phenyl group, wherein the phenyl group is of Formula IA where $R_6$, $R_7$, and $R_8$ are each independently hydrogen, methoxy, halo, or nitro; $R_9$ and $R_{10}$ are each independently hydrogen; $R_2$ is hydrogen; α is 1; Z is selected from the group consisting of

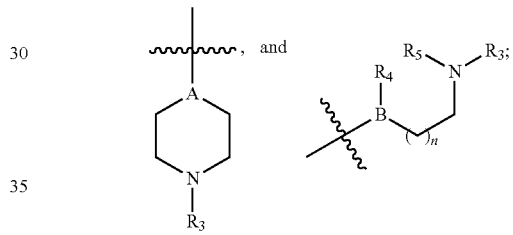

where $R_3$ is hydrogen or alkyl; $R_4$ and $R_5$ are each independently hydrogen, alkyl, cycloalkyl, or non-aromatic heterocyclyl; A is CH, C-alkyl, or N; B is CH, C-alkyl, or N; and n is 2 or 3.

In some embodiments, $R_6$ is hydrogen. In some embodiments, Z is

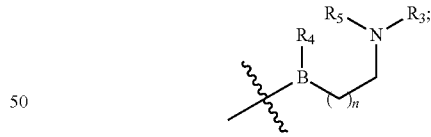

$R_3$ is methyl or ethyl, $R_4$ is methyl, and $R_5$ is hydrogen. In some embodiments, Z is

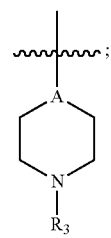

and $R_3$ is hydrogen. In some embodiments, W is CH. In some embodiments, $R_1$ is a phenyl group of Formula IA where $R_6$ is hydrogen; $R_7$, and $R_8$ are each independently hydrogen, methoxy, or halo; and $R_9$ and $R_{10}$ are each independently hydrogen.

In some embodiments, the compound is of Formula I.

In some embodiments, the compound is of Formulas II or III; $R_1$ is an alkyl group, an aralkyl group, a heteroaryl group, or a phenyl group, wherein the phenyl group is of Formula IA where $R_6R_7$, $R_8$, $R_9$ and $R_{10}$ are each independently hydrogen, halo, alkoxy, alkanoyl, carbamoyl, cyano, trifluoromethyl, or nitro. In some embodiments, the compound is of Formulas II or III, $R_1$ is an alkyl group, an aralkyl group, a heteroaryl group, or a phenyl group, wherein the phenyl group is of Formula IA where $R_6$, $R_7$, $R_9$, and $R_{10}$ are each independently hydrogen, halo, alkoxy, alkanoyl, carbamoyl, cyano, trifluoromethyl, or nitro; and $R_8$ is hydrogen, halo, substituted alkoxy, alkanoyl, carbamoyl, cyano, trifluoromethyl, or nitro.

In some embodiments, the compound is of Formulas II or III; $R_1$ is an alkyl group, an aralkyl group, a heteroaryl group, or a phenyl group, wherein the phenyl group is of Formula IA where $R_6$, $R_7$, $R_9$, and $R_{10}$ are each independently hydrogen, halo, alkoxy, alkanoyl, carbamoyl, cyano, trifluoromethyl, or nitro; and $R_8$ is hydrogen, halo, cycloalkoxy, alkanoyl, carbamoyl, cyano, trifluoromethyl, or nitro. In some embodiments, the compound is of Formulas II or III; $R_1$ is an alkyl group, an aralkyl group, a heteroaryl group, or a phenyl group, wherein the phenyl group is of Formula IA where $R_6$, $R_7$, $R_9$, and $R_{10}$ are each independently hydrogen, halo, alkoxy, alkanoyl, carbamoyl, cyano, trifluoromethyl, or nitro; and $R_8$ is hydrogen, halo, alkanoyl, carbamoyl, cyano, trifluoromethyl, or nitro.

In some embodiments, the compound is of Formulas II or III; $R_1$ is an alkyl group, an aralkyl group, a heteroaryl group, or a phenyl group, wherein the phenyl group is of Formula IA where $R_6$ $R_7$, $R_8$, $R_9$ and $R_{10}$ are each independently hydrogen, halo, alkanoyl, carbamoyl, cyano, trifluoromethyl, or nitro.

In some embodiments, the compound is of Formulas II or III; $R_1$ is an alkyl group, an aralkyl group, a heteroaryl group, or a phenyl group wherein the phenyl group is of Formula IA where $R_6$ is hydrogen, methoxy, halo, alkanoyl, or nitro; $R_7$ and $R_8$ are each independently hydrogen, alkoxy, aryloxy, halo, alkanoyl, or nitro; and $R_9$ and $R_{10}$ are each independently hydrogen. In some embodiments, the compound is of Formulas II or III; Y is O; $R_1$ is a heteroaryl group or a phenyl group, wherein the phenyl group is of Formula IA where $R_6R_7$, $R_8$, $R_9$ and $R_{10}$ are each independently hydrogen, halo, alkoxy, alkanoyl, carbamoyl, cyano, trifluoromethyl, or nitro; $R_2$ is hydrogen; α is 1; $R_4$ and $R_5$ are each independently hydrogen, alkyl, aryl, cycloalkyl, non-aromatic heterocyclyl, alkanoyl, or carbamoyl; and B is CH, C-alkyl, O, or N; with the provision that when B is O, $R_4$ is absent.

In some embodiments, the compound is of Formulas II or III; $X_2$ is hydrogen; Y is O; $R_1$ is an alkyl group, a substituted or unsubstituted benzyl group, a heteroaryl group, or a phenyl group wherein the phenyl group is of Formula IA where $R_6$ is hydrogen, methoxy, halo, alkanoyl, or nitro; $R_7$ and $R_8$ are each independently hydrogen, alkoxy, aryloxy, halo, alkanoyl, or nitro; $R_9$ and $R_{10}$ are each independently hydrogen; $R_2$ is hydrogen; α is 1; $R_4$ and $R_5$ are each independently hydrogen, alkyl, aryl, cycloalkyl, non-aromatic heterocyclyl, or alkanoyl; and B is CH, C-alkyl, or N.

In some embodiments, the compound is of Formulas II or III; $X_1$ is a halogen, a nitro group, a trifluoromethyl group, or a cyano group; $X_2$ is hydrogen; Y is O; $R_1$ is a methyl group, an ethyl group, a benzyl group, or a phenyl group, wherein the phenyl group is of Formula IA where $R_6$, $R_7$, and $R_8$ are each independently hydrogen, methoxy, halo, or nitro; $R_9$ and $R_{10}$ are each independently hydrogen; $R_2$ is hydrogen; α is 1; $R_4$ and $R_5$ are each independently hydrogen, alkyl, cycloalkyl, or non-aromatic heterocyclyl; B is CH, C-alkyl, or N.

In some embodiments, $R_6$ is hydrogen. In some embodiments, $R_3$ is methyl or ethyl; and $R_4$ is methyl. In some embodiments, W is CH. In some embodiments, $R_1$ is a phenyl group of Formula IA where $R_6$ is hydrogen; $R_7$, and $R_8$ are each independently hydrogen, methoxy, or halo; $R_9$ and $R_{10}$ are each independently hydrogen. In some embodiments, the compound is of Formula II. In some embodiments, the compound is of Formula III.

In some embodiments, the compound is:
2-((4-ethylpiperazin-1-yl)methyl)-6-nitro-3-phenylquinazolin-4(3H)-one,
6-nitro-3-phenyl-2-(piperazin-1-ylmethyl)quinazolin-4(3H)-one,
6-nitro-2-(piperazin-1-ylmethyl)-3-(thiophen-3-yl)quinazolin-4(3H)-one,
3-(2-fluorophenyl)-2-((4-methylpiperazin-1-yl)methyl)-6-nitroquinazolin-4(3H)-one,
2-((4-ethylpiperazin-1-yl)methyl)-3-(2-fluorophenyl)-6-nitroquinazolin-4(3H)-one,
2-((4-ethylpiperazin-1-yl)methyl)-3-(3-fluorophenyl)-6-nitroquinazolin-4(3H)-one, 2-((4-ethylpiperazin-1-yl)methyl)-3-(4-fluorophenyl)-6-nitroquinazolin-4(3H)-one,
3-(2-fluorophenyl)-2-((4-isopropylpiperazin-1-yl)methyl)-6-nitroquinazolin-4(3H)-one,
3-(2-fluorophenyl)-6-nitro-2-(piperazin-1-ylmethyl)quinazolin-4(3H)-one,
3-(2-fluorophenyl)-2-(morpholinomethyl)-6-nitroquinazolin-4(3H)-one,
3-(2-fluorophenyl)-6-nitro-2-(piperidin-1-ylmethyl)quinazolin-4(3H)-one,
3-(3-methoxyphenyl)-6-nitro-2-(piperazin-1-ylmethyl)quinazolin-4(3H)-one,
3-(4-methoxyphenyl)-6-nitro-2-(piperazin-1-ylmethyl)quinazolin-4(3H)-one,
2-((4-ethylpiperazin-1-yl)methyl)-6-iodo-3-phenylquinazolin-4(3H)-one,
2-((4-ethylpiperazin-1-yl)methyl)-4-oxo-3-phenyl-3,4-dihydroquinazoline-6-carbonitrile,
6-nitro-3-phenyl-2-((tetrahydropyrimidin-1(2H)-yl)methyl)quinazolin-4(3H)-one,
2-((1,4-diazepan-1-yl)methyl)-6-nitro-3-phenylquinazolin-4(3H)-one,
2-((methyl(2-(methylamino)ethyl)amino)methyl)-6-nitro-3-phenylquinazolin-4(3H)-one,
2-((methyl(3-(methylamino)propyl)amino)methyl)-6-nitro-3-phenylquinazolin-4(3H)-one,
2-(((2-(ethylamino)ethyl)(methyl)amino)methyl)-6-nitro-3-phenylquinazolin-4(3H)-one,
3-(4-methoxyphenyl)-2-((methyl(2-(methylamino)ethyl)amino)methyl)-6-nitroquinazolin-4(3H)-one,
3-(2-fluorophenyl)-2-((methyl(2-(methylamino)ethyl)amino)methyl)-6-nitroquinazolin-4(3H)-one,
3-(3-fluorophenyl)-2-((methyl(2-(methylamino)ethyl)amino)methyl)-4-oxo-3,4-dihydroquinazoline-6-carbonitrile,
6-fluoro-2-((methyl(2-(methylamino)ethyl)amino)methyl)-3-phenylquinazolin-4(3H)-one,
2-((methyl(2-(methylamino)ethyl)amino)methyl)-4-oxo-3-phenyl-3,4-dihydroquinazoline-6-carbonitrile, 2-((4-ethylpiperazin-1-yl)methyl)-6-nitro-3-phenylpyrido[2,3-d]pyrimidin-4(3H)-one,
6-nitro-3-phenyl-2-(piperidin-4-yl)quinazolin-4(3H)-one,
(E)-2-((1,4-dimethylpiperazin-2-ylidene)amino)-5-nitro-N-phenylbenzamide,
(E)-5-cyano-2-((1,4-dimethylpiperazin-2-ylidene)amino)-N-phenylbenzamide,
(E)-2-((1,4-dimethylpiperazin-2-ylidene)amino)-N-(4-methoxyphenyl)-5-nitrobenzamide,
(E)-2-((1,4-dimethylpiperazin-2-ylidene)amino)-N-(2-fluorophenyl)-5-nitrobenzamide,
(E)-4-chloro-5-cyano-2-((1,4-dimethylpiperazin-2-ylidene)amino)-N-phenylbenzamide,
(E)-2-((1-ethyl-4-methylpiperazin-2-ylidene)amino)-5-nitro-N-phenylbenzamide,
(E)-2-((1,4-dimethylpiperazin-2-ylidene)amino)-5-fluoro-N-phenylbenzamide,
(E)-5-cyano-2-((1,4-dimethylpiperazin-2-ylidene)amino)-N-(2-fluorophenyl)benzamide,
(E)-5-cyano-2-((1,4-dimethylpiperazin-2-ylidene)amino)-N-(3-fluorophenyl)benzamide,
(E)-2-((1,4-dimethylpiperazin-2-ylidene)amino)-N-(4-methoxyphenyl)-5-nitrobenzamide,
(E)-2-((1,4-dimethylpiperazin-2-ylidene)amino)-N-(3-fluorophenyl)-5-nitrobenzamide,
(E)-2-((1,4-dimethylpiperazin-2-ylidene)amino)-N-phenyl-5-(trifluoromethyl)benzamide,
(E)-2-((1,4-dimethylpiperazin-2-ylidene)amino)-N-(4-fluorophenyl)-5-nitrobenzamide,
(E)-2-((1,4-dimethylpiperazin-2-ylidene)amino)-N-(2-methoxyphenyl)-5-nitrobenzamide,
(E)-2-((1,4-dimethylpiperazin-2-ylidene)amino)-N-(3-methoxyphenyl)-5-nitrobenzamide,
(E)-2-((1,4-dimethylpiperazin-2-ylidene)amino)-N-isopropyl-5-nitrobenzamide,
(E)-N-benzyl-2-((1,4-dimethylpiperazin-2-ylidene)amino)-5-nitrobenzamide,
(E)-4-((1,4-dimethylpiperazin-2-ylidene)amino)-N-phenylpyridazine-3-carboxamide,
(E)-methyl 4-((1,4-dimethylpiperazin-2-ylidene)amino)-3-(phenylcarbamoyl)benzoate,
(E)-2-((1,4-dimethylpiperazin-2-ylidene)amino)-5-nitro-N-(thiophen-3-yl)benzamide,
(E)-2-((1,4-dimethylpiperazin-2-ylidene)amino)-4,5-difluoro-N-phenylbenzamide,
(E)-5-cyano-2-((1,4-dimethylpiperazin-2-ylidene)amino)-4-fluoro-N-phenylbenzamide,
(E)-2-((1,4-dimethylpiperazin-2-ylidene)amino)-N-methyl-5-nitrobenzamide,
(Z)-2-((1,4-dimethylpiperazin-2-ylidene)amino)-5-nitro-N-phenylbenzamide,
(Z)-5-cyano-2-((1,4-dimethylpiperazin-2-ylidene)amino)-N-phenylbenzamide,
(Z)-2-((1,4-dimethylpiperazin-2-ylidene)amino)-N-(4-methoxyphenyl)-5-nitrobenzamide,
(Z)-2-((1,4-dimethylpiperazin-2-ylidene)amino)-N-(2-fluorophenyl)-5-nitrobenzamide,
(Z)-4-chloro-5-cyano-2-((1,4-dimethylpiperazin-2-ylidene)amino)-N-phenylbenzamide,
(Z)-2-((1-ethyl-4-methylpiperazin-2-ylidene)amino)-5-nitro-N-phenylbenzamide,
(Z)-2-((1,4-dimethylpiperazin-2-ylidene)amino)-5-fluoro-N-phenylbenzamide,
(Z)-5-cyano-2-((1,4-dimethylpiperazin-2-ylidene)amino)-N-(2-fluorophenyl)benzamide,
(Z)-5-cyano-2-((1,4-dimethylpiperazin-2-ylidene)amino)-N-(3-fluorophenyl)benzamide,
(Z)-2-((1,4-dimethylpiperazin-2-ylidene)amino)-N-(4-methoxyphenyl)-5-nitrobenzamide,
(Z)-2-((1,4-dimethylpiperazin-2-ylidene)amino)-N-(3-fluorophenyl)-5-nitrobenzamide,
(Z)-2-((1,4-dimethylpiperazin-2-ylidene)amino)-N-phenyl-5-(trifluoromethyl)benzamide,
(Z)-2-((1,4-dimethylpiperazin-2-ylidene)amino)-N-(4-fluorophenyl)-5-nitrobenzamide,
(Z)-2-((1,4-dimethylpiperazin-2-ylidene)amino)-N-(2-methoxyphenyl)-5-nitrobenzamide,
(Z)-2-((1,4-dimethylpiperazin-2-ylidene)amino)-N-(3-methoxyphenyl)-5-nitrobenzamide,
(Z)-2-((1,4-dimethylpiperazin-2-ylidene)amino)-N-isopropyl-5-nitrobenzamide,
(Z)—N-benzyl-2-((1,4-dimethylpiperazin-2-ylidene)amino)-5-nitrobenzamide,
(Z)-4-((1,4-dimethylpiperazin-2-ylidene)amino)-N-phenylpyridazine-3-carboxamide,
(Z)-methyl 4-((1,4-dimethylpiperazin-2-ylidene)amino)-3-(phenylcarbamoyl)benzoate,
(Z)-2-((1,4-dimethylpiperazin-2-ylidene)amino)-5-nitro-N-(thiophen-3-yl)benzamide,
(Z)-2-((1,4-dimethylpiperazin-2-ylidene)amino)-4,5-difluoro-N-phenylbenzamide,
(Z)-5-cyano-2-((1,4-dimethylpiperazin-2-ylidene)amino)-4-fluoro-N-phenylbenzamide, or
(Z)-2-((1,4-dimethylpiperazin-2-ylidene)amino)-N-methyl-5-nitrobenzamide.

In some embodiments, the compound is
(E)-2-((1,4-dimethylpiperazin-2-ylidene)amino)-5-nitro-N-phenylbenzamide,
(E)-5-cyano-2-((1,4-dimethylpiperazin-2-ylidene)amino)-N-phenylbenzamide,
(E)-2-((1,4-dimethylpiperazin-2-ylidene)amino)-N-(4-methoxyphenyl)-5-nitrobenzamide,
(E)-2-((1,4-dimethylpiperazin-2-ylidene)amino)-N-(2-fluorophenyl)-5-nitrobenzamide,
(E)-4-chloro-5-cyano-2-((1,4-dimethylpiperazin-2-ylidene)amino)-N-phenylbenzamide,
(E)-2-((1-ethyl-4-methylpiperazin-2-ylidene)amino)-5-nitro-N-phenylbenzamide,
(E)-2-((1,4-dimethylpiperazin-2-ylidene)amino)-5-fluoro-N-phenylbenzamide,
(E)-5-cyano-2-((1,4-dimethylpiperazin-2-ylidene)amino)-N-(2-fluorophenyl)benzamide,
(E)-5-cyano-2-((1,4-dimethylpiperazin-2-ylidene)amino)-N-(3-fluorophenyl)benzamide,
(E)-2-((1,4-dimethylpiperazin-2-ylidene)amino)-N-(4-methoxyphenyl)-5-nitrobenzamide,
(E)-2-((1,4-dimethylpiperazin-2-ylidene)amino)-N-(3-fluorophenyl)-5-nitrobenzamide,
(E)-2-((1,4-dimethylpiperazin-2-ylidene)amino)-N-phenyl-5-(trifluoromethyl)benzamide,
(E)-2-((1,4-dimethylpiperazin-2-ylidene)amino)-N-(4-fluorophenyl)-5-nitrobenzamide,
(E)-2-((1,4-dimethylpiperazin-2-ylidene)amino)-N-(2-methoxyphenyl)-5-nitrobenzamide,
(E)-2-((1,4-dimethylpiperazin-2-ylidene)amino)-N-(3-methoxyphenyl)-5-nitrobenzamide,
(E)-2-((1,4-dimethylpiperazin-2-ylidene)amino)-N-isopropyl-5-nitrobenzamide,
(E)-N-benzyl-2-((1,4-dimethylpiperazin-2-ylidene)amino)-5-nitrobenzamide,
(E)-4-((1,4-dimethylpiperazin-2-ylidene)amino)-N-phenylpyridazine-3-carboxamide,
(E)-methyl 4-((1,4-dimethylpiperazin-2-ylidene)amino)-3-(phenylcarbamoyl)benzoate, (E)-2-((1,4-dimethylpiperazin-2-ylidene)amino)-5-nitro-N-(thiophen-3-yl)benzamide,
(E)-2-((1,4-dimethylpiperazin-2-ylidene)amino)-4,5-difluoro-N-phenylbenzamide,
(E)-5-cyano-2-((1,4-dimethylpiperazin-2-ylidene)amino)-4-fluoro-N-phenylbenzamide, or
(E)-2-((1,4-dimethylpiperazin-2-ylidene)amino)-N-methyl-5-nitrobenzamide.

In some embodiments, the compound is
2-((4-ethylpiperazin-1-yl)methyl)-6-nitro-3-phenylquinazolin-4(3H)-one,
6-nitro-3-phenyl-2-(piperazin-1-ylmethyl)quinazolin-4(3H)-one,
6-nitro-2-(piperazin-1-ylmethyl)-3-(thiophen-3-yl)quinazolin-4(3H)-one,
3-(2-fluorophenyl)-2-((4-methylpiperazin-1-yl)methyl)-6-nitroquinazolin-4(3H)-one,
2-((4-ethylpiperazin-1-yl)methyl)-3-(2-fluorophenyl)-6-nitroquinazolin-4(3H)-one,
2-((4-ethylpiperazin-1-yl)methyl)-3-(3-fluorophenyl)-6-nitroquinazolin-4(3H)-one, 2-((4-ethylpiperazin-1-yl)methyl)-3-(4-fluorophenyl)-6-nitroquinazolin-4(3H)-one,
3-(2-fluorophenyl)-2-((4-isopropylpiperazin-1-yl)methyl)-6-nitroquinazolin-4(3H)-one,
3-(2-fluorophenyl)-6-nitro-2-(piperazin-1-ylmethyl)quinazolin-4(3H)-one,
3-(2-fluorophenyl)-2-(morpholinomethyl)-6-nitroquinazolin-4(3H)-one,
3-(2-fluorophenyl)-6-nitro-2-(piperidin-1-ylmethyl)quinazolin-4(3H)-one,
3-(3-methoxyphenyl)-6-nitro-2-(piperazin-1-ylmethyl)quinazolin-4(3H)-one,
3-(4-methoxyphenyl)-6-nitro-2-(piperazin-1-ylmethyl)quinazolin-4(3H)-one,
2-((4-ethylpiperazin-1-yl)methyl)-6-iodo-3-phenylquinazolin-4(3H)-one,
2-((4-ethylpiperazin-1-yl)methyl)-4-oxo-3-phenyl-3,4-dihydroquinazoline-6-carbonitrile,
6-nitro-3-phenyl-2-((tetrahydropyrimidin-1(2H)-yl)methyl)quinazolin-4(3H)-one,
2-((1,4-diazepan-1-yl)methyl)-6-nitro-3-phenylquinazolin-4(3H)-one,
2-((methyl(2-(methylamino)ethyl)amino)methyl)-6-nitro-3-phenylquinazolin-4(3H)-one,
2-((methyl(3-(methylamino)propyl)amino)methyl)-6-nitro-3-phenylquinazolin-4(3H)-one,
2-(((2-(ethylamino)ethyl)(methyl)amino)methyl)-6-nitro-3-phenylquinazolin-4(3H)-one,
3-(4-methoxyphenyl)-2-((methyl(2-(methylamino)ethyl)amino)methyl)-6-nitroquinazolin-4(3H)-one,
3-(2-fluorophenyl)-2-((methyl(2-(methylamino)ethyl)amino)methyl)-6-nitroquinazolin-4(3H)-one,
3-(3-fluorophenyl)-2-((methyl(2-(methylamino)ethyl)amino)methyl)-4-oxo-3,4-dihydroquinazoline-6-carbonitrile,
6-fluoro-2-((methyl(2-(methylamino)ethyl)amino)methyl)-3-phenylquinazolin-4(3H)-one,
2-((methyl(2-(methylamino)ethyl)amino)methyl)-4-oxo-3-phenyl-3,4-dihydroquinazoline-6-carbonitrile,
2-((4-ethylpiperazin-1-yl)methyl)-6-nitro-3-phenylpyrido[2,3-d]pyrimidin-4(3H)-one, or
6-nitro-3-phenyl-2-(piperidin-4-yl)quinazolin-4(3H)-one.

In some embodiments, the compound is:
(Z)-2-((1,4-dimethylpiperazin-2-ylidene)amino)-5-nitro-N-phenylbenzamide,
(Z)-5-cyano-2-((1,4-dimethylpiperazin-2-ylidene)amino)-N-phenylbenzamide,
(Z)-2-((1,4-dimethylpiperazin-2-ylidene)amino)-N-(4-methoxyphenyl)-5-nitrobenzamide,
(Z)-2-((1,4-dimethylpiperazin-2-ylidene)amino)-N-(2-fluorophenyl)-5-nitrobenzamide,
(Z)-4-chloro-5-cyano-2-((1,4-dimethylpiperazin-2-ylidene)amino)-N-phenylbenzamide,
(Z)-2-((1-ethyl-4-methylpiperazin-2-ylidene)amino)-5-nitro-N-phenylbenzamide,
(Z)-2-((1,4-dimethylpiperazin-2-ylidene)amino)-5-fluoro-N-phenylbenzamide,
(Z)-5-cyano-2-((1,4-dimethylpiperazin-2-ylidene)amino)-N-(2-fluorophenyl)benzamide,
(Z)-5-cyano-2-((1,4-dimethylpiperazin-2-ylidene)amino)-N-(3-fluorophenyl)benzamide,
(Z)-2-((1,4-dimethylpiperazin-2-ylidene)amino)-N-(4-methoxyphenyl)-5-nitrobenzamide,
(Z)-2-((1,4-dimethylpiperazin-2-ylidene)amino)-N-(3-fluorophenyl)-5-nitrobenzamide,
(Z)-2-((1,4-dimethylpiperazin-2-ylidene)amino)-N-phenyl-5-(trifluoromethyl)benzamide,
(Z)-2-((1,4-dimethylpiperazin-2-ylidene)amino)-N-(4-fluorophenyl)-5-nitrobenzamide,
(Z)-2-((1,4-dimethylpiperazin-2-ylidene)amino)-N-(2-methoxyphenyl)-5-nitrobenzamide,
(Z)-2-((1,4-dimethylpiperazin-2-ylidene)amino)-N-(3-methoxyphenyl)-5-nitrobenzamide,
(Z)-2-((1,4-dimethylpiperazin-2-ylidene)amino)-N-isopropyl-5-nitrobenzamide,
(Z)—N-benzyl-2-((1,4-dimethylpiperazin-2-ylidene)amino)-5-nitrobenzamide,
(Z)-4-((1,4-dimethylpiperazin-2-ylidene)amino)-N-phenylpyridazine-3-carboxamide,
(Z)-methyl 4-((1,4-dimethylpiperazin-2-ylidene)amino)-3-(phenylcarbamoyl)benzoate,
(Z)-2-((1,4-dimethylpiperazin-2-ylidene)amino)-5-nitro-N-(thiophen-3-yl)benzamide,
(Z)-2-((1,4-dimethylpiperazin-2-ylidene)amino)-4,5-difluoro-N-phenylbenzamide,
(Z)-5-cyano-2-((1,4-dimethylpiperazin-2-ylidene)amino)-4-fluoro-N-phenylbenzamide, or
(Z)-2-((1,4-dimethylpiperazin-2-ylidene)amino)-N-methyl-5-nitrobenzamide.

In another aspect, the present technology provides a method comprising administering to a subject in need thereof an antiviral effective amount of a compound of Formulas I, II, or III. In the method, risk of infection by and/or transmission of an alphavirus by said subject is decreased.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment or prophylaxis of an encephalitic alphavirus. Another example of an effective amount includes amounts or dosages that are capable of reducing symptoms associated with an encephalitic alphavirus, such as, for example, fever, headache, and encephalitis.

As used herein, a "subject" or "patient" is a mammal, such as a cat, dog, rodent or primate. Typically the subject is a human, and, preferably, a human suspected of having a disease associated with an alphavirus. The term "subject" and "patient" can be used interchangeably.

In another aspect, a composition is provided including a compound of Formulas I, II, or III and a pharmaceutically acceptable carrier. In a related aspect, a pharmaceutical composition is provided for treating a viral infection, where the composition includes an effective amount of the compound of Formulas I, II, or III. In some embodiments, the viral infection comprises an alphavirus. In some embodiments, the viral infection comprises an encephalitic alphavirus. In some embodiments, the viral infection comprises a Venezuelan equine encephalitis virus. In some embodiments, the effective compound selectively treats the viral infection. Thus, the instant present technology provides pharmaceutical compositions and medicaments comprising any of the compounds disclosed herein (e.g., compounds of Formulas I, II, or III) and a pharmaceutically acceptable carrier or one or more excipients or fillers. The compositions may be used in the methods and treatments described herein. Such compositions include a viral inhibitory effective amount of any compound as described herein, including but not limited to a compound of Formulas I, II, or III. In some embodiments, the pharmaceutical composition is packaged in unit dosage form. The unit dosage form is effective in preventing infection by, reducing symptoms associated with, and/or reducing risk of transmission of an encephalitic alphavirus when administered to a subject in need thereof.

The pharmaceutical compositions may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to prevent and treat disorders associated with the effects of increased plasma and/or hepatic lipid levels. The compounds and compositions described herein may be used to prepare formulations and medicaments that prevent or treat a variety of disorders associated with an encephalitic alphavirus. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until the elevated plasma or elevated white blood cell count or hepatic cholesterol or triglycerides or progression of the disease state is decreased or stopped. The progression of the disease state can be assessed using in vivo imaging, as described, or by taking a tissue sample from a patient and observing the target of interest therein. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the viral treatment according to the present technology.

Effectiveness of the compositions and methods of the present technology may also be demonstrated by a decrease in the symptoms of an encephalitic alphavirus, such as, for example, fever, headache, and encephalitis.

For each of the indicated conditions described herein, test subjects will exhibit a 10%, 20%, 30%, 50% or greater reduction, up to a 75-90%, or 95% or greater, reduction, in one or more symptom(s) caused by, or associated with, viral infection in the subject, compared to placebo-treated or other suitable control subjects.

The compounds of the present technology can also be administered to a patient along with other conventional therapeutic agents that may be useful in the treatment or prophylaxis of viral infection. In one aspect, a method is provided for administering to a subject in need thereof an antiviral effective amount of a compound of the present technology. A subject in need thereof may be a patient suffering from or believed to be at risk of suffering from a disease associated with a virus, such as an encephalitic alphavirus. In some embodiments, the compound is effective in the treatment of an alphavirus. In some embodiments, the compound is effective in the treatment of an encephalitic alphavirus. In some embodiments, the compound is effective in the treatment of a Venezuelan equine encephalitis virus. In some embodiments, the compound selectively treats the viral infection. In some embodiments, the risk of infection by and/or transmission of an alphavirus by said subject is decreased. In any of these embodiments, the administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment or prophylaxis of encephalitic alphavirus. Exemplary therapeutic agents for use in combination therapies with one or more compounds of the present technology include, but are not limited to, other antiviral therapeutics, antibiotics, and anti-inflammatory drugs.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, VEEV nsP2 helicase. Suitable labels are known by those skilled in the art and can include, for example, radioisotopes, radionuclides, isotopes, fluorescent groups, biotin (in conjunction with streptavidin complexation), and chemoluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

Examples

General Synthetic and Analytical Details:

$^1$H and $^{13}$C NMR spectra were recorded on a Bruker AM 400 spectrometer (operating at 400 and 101 MHz respectively) or a Bruker AVIII spectrometer (operating at 500 and 126 MHz respectively) in CDCl$_3$ with 0.03% TMS as an internal standard or DMSO-d$_6$. The chemical shifts (δ) reported are given in parts per million (ppm) and the coupling constants (J) are in Hertz (Hz). The spin multiplicities are reported as s=singlet, bs=broad singlet, d=doublet, t=triplet, q=quartet, dd=doublet of doublet and m=multiplet. The LCMS analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 um column; UV detection wavelength=214 nm; flow rate=0.4 ml/min; gradient=5-100% acetonitrile over 3 minutes with a hold of 0.8 minutes at 100% acetonitrile; the aqueous mobile phase contained 0.15% ammonium hydroxide (v/v). The mass spectrometer utilized the following parameters: an Agilent multimode source which simultaneously acquires ESI+/APCI+; α reference mass solution consisting of purine and hexakis(1H,1H,3H-tetrafluoropropoxy) phosphazine; and a make-up solvent of 90:10:0.1 MeOH:Water:Formic Acid which was introduced to the LC flow prior to the source to assist ionization. Melting points were determined on a Stanford Research Systems OptiMelt apparatus.

Synthesis of (E)-2-((1,4-dimethylpiperazin-2-ylidene)amino)-5-nitro-N-phenylbenzamide ("ML336")

A general synthetic scheme is shown in Scheme 1, followed by a detailed description of the synthesis of ML336.

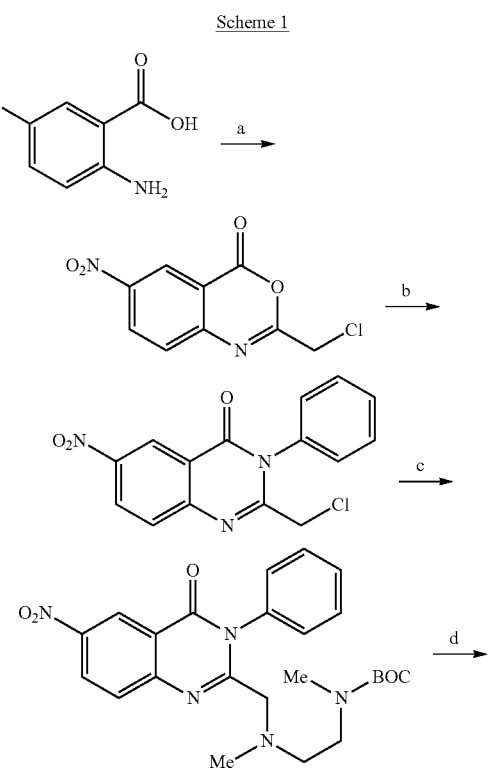

Scheme 1

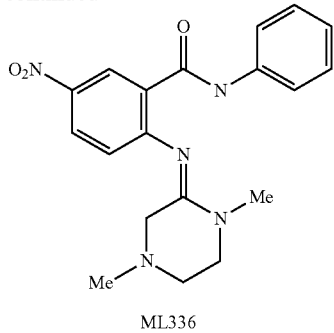

ML336 a) ClCOCH₂Cl, NEt₃, DCM, 0° C. to rt, 100%; b) PhNH₂, POCl₃, MeCN, MWI, 150° C., 64%; c) MeHNCH₂CH₂NMeBoc, KI, K₂CO₃, MeCN, MWI, 80° C., 35%; d) TFA/CH₂Cl₂, rt, 49%.

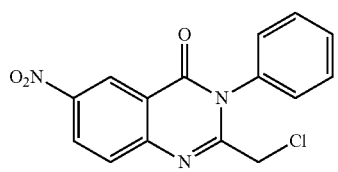 [SMILES: O=c1c2cc([N+](=O)[O-])ccc2nc(CCl)n1-c1ccccc1]

Synthesis of 2-(chloromethyl)-6-nitro-4H-benzo[d][1,3]oxazin-4-one 2-amino-5-nitro-benzoic acid (6.718 g, 36.9 mmol, 1 eq.) was placed under nitrogen and dissolved in CH₂Cl₂ (100 mL). After addition of triethylamine (5.9 mL, 42.3 mmol, 1.15 eq), the mixture was lowered to 0° C. in an ice bath and a solution of chloroacetyl chloride (3.2 mL, 40.2 mmol, 1.1 eq) in CH₂Cl₂ (50 mL) was slowly added. The reaction mixture was stirred at 0° C. for 1 hour, then at rt for 1 additional hour. The solvent was removed in vacuo and water was added to the remaining solid. The solid was filtered and rinsed with water (3×20 mL), followed by 5% Et₂O/Hexanes (3×30 mL) to give 2-(chloromethyl)-6-nitro-4H-benzo[d][1,3]oxazin-4-one (8.87 g, 100%) along with residual triethylamine as a pale, yellow solid. The product was used in the following step without further purification. ¹H NMR (400 MHz, acetone-d₆) δ 8.96-8.91 (m, 2H), 8.48 (dd, J=9.3, 2.8 Hz, 1H), 4.44 (s, 2H).

2-(chloromethyl)-6-nitro-3-phenylquinazolin-4(3H)-one. To a microwave vial was added 2-(chloromethyl)-6-nitro-4H-benzo[d][1,3]oxazin-4-one (1.47 g, 6.12 mmol, 1 eq) under Ar, and the solid was dissolved in acetonitrile (13 mL). Phosphorus oxychloride (1.15 mL, 12.34 mmol, 2 eq) was added, followed by the addition of solution of aniline (0.73 mL, 8.00 mmol, 1.3 eq) in acetonitrile (4 mL). The mixture was heated in a MW reactor at 150° C. for 15 min. The reaction mixture was transferred to a larger flask and slowly quenched with saturated aq. NaHCO₃ (20 mL). The precipitate was filtered and rinsed with water (3×20 mL) to give 2-(chloromethyl)-6-nitro-3-phenylquinazolin-4(3H)-one (1.24 g, 64%) as a burnt-orange solid. ¹H NMR (400 MHz, CDCl₃) δ 9.13 (d, J=2.6 Hz, 1H), 8.59 (dd, J=8.9, 2.6 Hz, 1H), 7.91 (d, J=9.0 Hz, 1H), 7.65-7.58 (m, 3H), 7.39-7.35 (m, 2H), 4.28 (s, 2H).

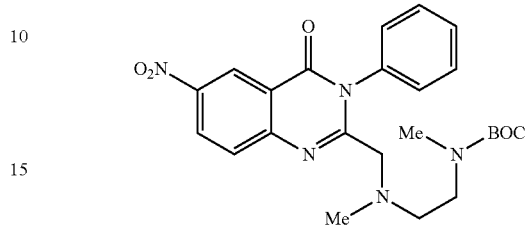

tert-butyl-methyl(2-(methyl((6-nitro-4-oxo-3-phenyl-3,4-dihydroquinazolin-2-yl)methyl)amino)ethyl)carbamate 2-(chloromethyl)-6-nitro-3-phenylquinazolin-4(3H)-one (1.40 g, 4.43 mmol, 1 eq) was dissolved in acetonitrile (18 mL). Potassium carbonate (1.226 g, 8.87 mmol, 2 eq), tert-butyl methyl(2-(methylamino)ethyl)carbamate (ChemBridge, 1.18 g, 6.25 mmol, 1.4 eq), and potassium iodide (0.280 g, 1.687 mmol, 0.4 eq) were added sequentially, and the mixture was heated in a MW reactor at 80° C. for 5 min. The crude reaction mixture was adsorbed onto Celite®, and the product was purified (2×) by flash chromatography (CombiFlash, 40 g silica, 0-10% MeOH/CH₂Cl₂, followed by CombiFlash, 80 g silica, 0-80% EtOAc/Hexanes) to give tert-butyl-methyl(2-(methyl((6-nitro-4-oxo-3-phenyl-3,4-dihydroquinazolin-2-yl)methyl)amino)ethyl)carbamate (0.72 g, 35%) as a pale orange solid. ¹H NMR (400 MHz, CDCl₃) δ 9.13 (d, J=2.6 Hz, 1H), 8.56 (dd, J=9.0, 2.7 Hz, 1H), 7.89 (d, J=9.0 Hz, 1H), 7.60-7.52 (m, 3H), 7.32-7.27 (m, 2H), 3.36 (s, 2H), 3.14 (br d, J=19.4 Hz, 2H), 2.75 (br s, 3H), 2.48 (br s, 2H), 2.20 (s, 3H), 1.39 (br s, 9H).

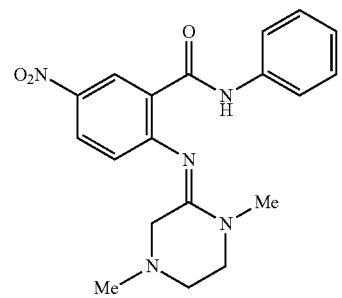

(E)-2-((1,4-dimethylpiperazin-2-ylidene)amino)-5-nitro-N-phenylbenzamide ("ML336")

To a stirred solution of tert-butyl methyl(2-(methyl((6-nitro-4-oxo-3-phenyl-3,4-dihydroquinazolin-2-yl)methyl)amino)ethyl)carbamate (678 mg, 1.45 mmol) in CH₂Cl₂ (20 mL), TFA (9.5 mL, 124 mmol) was slowly added, and the resulting mixture was stirred at rt for 45 min. Water (40 mL) and CH₂Cl₂ (40 mL) were then added, and the mixture was adjusted to pH 10 using saturated aq. Na₂CO₃ (40 mL). The organic phase was separated and the aqueous layer was extracted with CH$_2$Cl$_2$ (2×40 mL). The combined organic phase was concentrated and purified by flash chromatography (CombiFlash, 40 g silica, 0-5% MeOH/CH$_2$Cl$_2$) to give the product (265 mg, 49%) as a pale yellow solid. $^1$H NMR (500 MHz, CDCl$_3$) δ 10.99 (s, 1H), 9.15 (d, J=2.8 Hz, 1H), 8.15 (dd, J=8.8, 2.8 Hz, 1H), 7.65-7.60 (m, 2H), 7.38-7.33 (m, 2H), 7.12 (tt, J=7.3, 1.2 Hz, 1H), 6.80 (d, J=8.8 Hz, 1H), 3.47 (t, J=5.7 Hz, 2H), 3.28 (s, 3H), 3.13 (s, 2H), 2.69 (t, J=5.7 Hz, 2H), 2.26 (s, 3H). $^{13}$C NMR (126 MHz, CDCl$_3$) δ 162.63, 156.42, 153.97, 142.79, 138.19, 129.09, 127.64, 126.35, 126.16, 124.19, 123.75, 120.19, 55.12, 51.82, 49.66, 45.27, 36.88. LCMS retention time: 3.206 min, purity at 214 nm=99.2%. HRMS m/z calculated for C$_{19}$H$_{22}$N$_5$O$_3$ [M$^+$+H] 368.1723. found 368.1718. Pale yellow needles, mp 168-173° C. (recrystallized from CH$_2$Cl$_2$).

While the product was initially logged as 2-((methyl(2-(methylamino)ethyl)amino)methyl)-6-nitro-3-phenylquinazolin-4(3H)-one, upon inspection of the $^1$H NMR and $^{13}$C NMR it was clear that (E)-2-((1,4-dimethylpiperazin-2-ylidene)amino)-5-nitro-N-phenylbenzamide was formed (265 mg, 49%) as a pale yellow solid. Particularly telling was the singlet at δ 10.99 corresponding to 1 hydrogen atom. While this was the proton bonded to the nitrogen, it was at a significantly higher shift than would be expected for a secondary amine. Such a shift is normally seen in amide protons where the amide nitrogen is further conjugated with an aromatic ring. Similarly, the E configuration appeared to be the correct isomer due not only to allylic strain considerations, but also to the absence of higher order splitting of the proton ortho to the aromatic carbon bearing the sp$^2$ amidine nitrogen and the protons of the methyl group on the sp$^3$ amidine nitrogen, as would likely be observed with the Z isomer. Due to this and other considerations known to those of ordinary skill in the art, it was apparent that (E)-2-((1,4-dimethylpiperazin-2-ylidene)amino)-5-nitro-N-phenylbenzamide was the product.

The structural connectivity of ML336 was further confirmed using 2D proton-carbon HSQC and HMBC correlations, in conjunction with the above $^1$H and $^{13}$C NMR shifts (Diagrams 1 and 2).

Diagram 1. Correlation Assignments

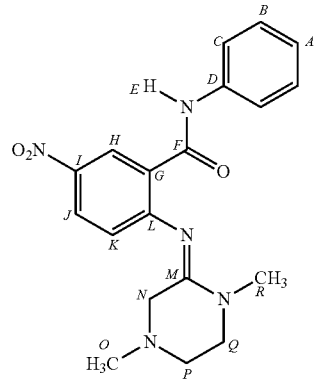

| Position | $^1$H NMR σ | $^{13}$C NMR σ |
| --- | --- | --- |
| A | 7.12 (tt, J = 7.3, 1.2 Hz, 1H) | 124.19 |
| B | 7.38-7.33 (m, 2H) | 129.09 |
| C | 7.65-7.60 (m, 2H) | 120.19 |
| D |  | 138.19 |
| E | 10.99 (s, 1H) |  |
| F |  | 162.63 |
| G |  | 126.16 |
| H | 9.15 (d, J = 2.8 Hz, 1H) | 127.64 |
| I |  | 142.79 |
| J | 8.15 (dd, J = 8.8, 2.8 Hz, 1H) | 126.35 |
| K | 6.80 (d, J = 8.8 Hz, 1H) | 123.75 |
| L |  | 153.97 |
| M |  | 156.42 |
| N | 3.13 (s, 2H) | 55.12 |
| O | 2.26 (s, 3H) | 45.27 |
| P | 2.69 (t, J = 5.7 Hz, 2H) | 51.82 |
| Q | 3.47 (t, J = 5.7 Hz, 2H) | 49.66 |
| R | 3.28 (s, 3H) | 36.88 |

The NOESY data showed a weak NOE between the protons of the amidine methyl group and the ortho-situated aromatic proton of the amide phenyl group (labeled R and C, respectively, Diagram 2). Additionally, a strong NOE was observed between the methylene protons alpha to the amidine group and the ortho-positioned aromatic proton of the core (labeled N and K, respectively, Diagram 2). Taken together, these data further support the assignment of the E-stereochemistry of ML336.

Diagram 2. NOESY Data

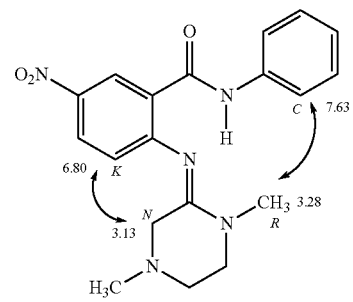

(E)-2-((1,4-dimethylpiperazin-2-ylidene)amino)-5-nitro-N-phenylbenzamide
Supported by 2D NOESY Data

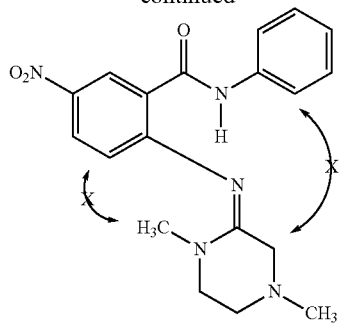

(Z)-2-((1,4-dimethylpiperazin-2-ylidene)amino)-5-nitro-
N-phenylbenzamide
NOT supported by 2D NOESY Data Furthermore, it is expected that (Z)-2-((1,4-dimethylpiperazin-2-ylidene)amino)-5-nitro-N-phenylbenzamide (as well as those compounds of Formula III where $R_3$ is not hydrogen) will readily isomerize to the corresponding E isomer in conditions facilitating proton transfer, such as physiological conditions, protic solvents, and aprotic polar solvents, including acid/base catalyzed conditions. Without being bound by theory, this expectation is founded not only on the allylic strain of such systems, but also on the basicity of the amidine, the acidity of the amide, and the experimental results provided herein.

Chemical Stability of ML336:

ML336 was evaluated for susceptibility to nucleophilic addition and formation of conjugates by treatment with dithiothreitol (DTT). FIG. 1 represents the time course experiment with ML336 under various conditions. ML336 was dissolved at 10 μM in PBS at pH 7.4 (1% DMSO) and independently incubated at room temperature with no nucleophile present or 50 μM dithiothreitol (DTT). The test reactions were sampled every hour for eight hours and analyzed by LCMS. The analytical LCMS system utilized for the analysis was a Waters Acquity system with UV-detection and mass-detection (Waters LCT Premier). The analytical method conditions included a Waters Acquity HS S T3 C18 column (2.1×50 mm, 1.8 μm) and elution with a linear gradient of 1% water to 100% $CH_3CN$ at 0.6 mL/min flow rate. Peaks on the 214 nm chromatographs were integrated using the Waters OpenLynx software. Absolute areas under the curve were compared at each time point to determine relative percent parent remaining. The masses of potential adducts and dimers of ML336 were searched for in the final samples to determine if any detectable adduct formed or dimerization had occurred. All samples were prepared in duplicate. Ethacrynic acid, a known Michael acceptor, was used as a positive control. In the case of ML336, no adducts were detected at any time point using LCMS detection.

Table 1 summarizes the percent remaining of ML336 at the endpoints of each run in each experiment.

TABLE 1

| Test Condition | Run | Percent ML336 Remaining after 8 h | Averaged Percent ML336 Remaining after 8 h |
|---|---|---|---|
| ML336 without nucleophile (control) | 1 | 96.13 | 93.92 |

TABLE 1-continued

| Test Condition | Run | Percent ML336 Remaining after 8 h | Averaged Percent ML336 Remaining after 8 h |
|---|---|---|---|
| ML336 without nucleophile (control) | 2 | 91.70 | |
| ML336 with 5X DTT | 1 | 100.36 | 98.96 |
| ML336 with 5X DTT | 2 | 97.55 | |

Synthesis of (E)-2-((1,4-dimethylpiperazin-2-ylidene)amino)-N-(4-methoxyphenyl)-5-nitrobenzamide

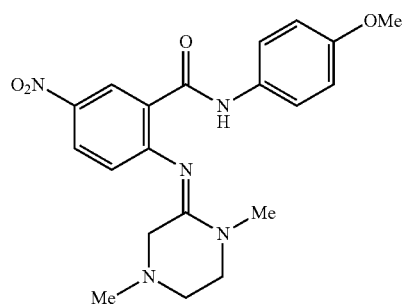 [SMILES: COc1ccc(NC(=O)c2cc([N+](=O)[O-])ccc2/N=C2\CN(C)CCN2C)cc1]

(E)-2-((1,4-dimethylpiperazin-2-ylidene)amino)-N-(4-methoxyphenyl)-5-nitrobenzamide (E)-2-((1,4-dimethylpiperazin-2-ylidene)amino)-N-(4-methoxyphenyl)-5-nitrobenzamide was synthesized according to a slight modification of the above procedures. To a stirred solution of tert-butyl (2-(((3-(4-methoxyphenyl)-6-nitro-4-oxo-3,4-dihydroquinazolin-2-yl)methyl)(methyl)amino)ethyl)(methyl)carbamate (250 mg, 0.50 mmol) in $CH_2Cl_2$ (10 mL) was slowly added TFA (0.39 mL, 5.02 mmol). The mixture was stirred at rt for 3 h, and then the reaction was quenched with saturated solution of $NaHCO_3$. The organic phase was separated and the aqueous layer was extracted with $CH_2Cl_2$ (2×20 mL). The combined organic phase was dried with anhydrous $Na_2SO_4$, concentrated, and purified by flash chromatography (CombiFlash, 24 g silica, 0-5% MeOH/$CH_2Cl_2$) to give (E)-2-((1,4-dimethylpiperazin-2-ylidene)amino)-N-(4-methoxyphenyl)-5-nitrobenzamide (96 mg, 48%) as a yellow solid. $^1H$ NMR (400 MHz, $CDCl_3$) δ 10.9 (s, 1H), 9.14 (d, J=2.8 Hz, 1H), 8.13 (dd, J=8.8, 2.8 Hz, 1H), 7.54-7.52 (m, 2H), 6.90-6.88 (m, 2H), 6.79 (d, J=8.8 Hz, 1H), 3.80 (s, 3H), 3.47 (t, J=5.4 Hz, 2H), 3.26 (s, 3H), 3.13 (s, 2H), 2.69 (t, J=5.7 Hz, 2H), 2.26 (s, 3H). $^{13}C$ NMR (101 MHz, $CDCl_3$) δ 162.52, 156.53, 156.42, 154.05, 142.93, 131.53, 127.68, 126.41, 126.36, 123.84, 121.86, 121.86, 114.40, 77.55, 77.23, 76.91, 55.66, 55.29, 52.00, 49.83, 45.43, 37.03. LCMS retention time: 3.169 min, purity at 254 nm=99.4%. HRMS m/z calculated for $C_{19}H_{22}N_5O_3$ [M$^+$+H] 398.1828. found 388.1840.

Synthesis of (E)-5-cyano-2-((1,4-dimethylpiperazin-2-ylidene)amino)-N-phenylbenzamide

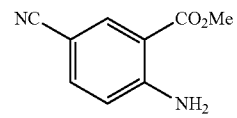

Methyl 2-amino-5-cyanobenzoate

Palladium (II) acetate (0.063 g, 0.28 mmol, 0.1 eq), DPPF (0.16 g, 0.28 mmol, 0.1 eq), K$_2$CO$_3$ (1.16 g, 8.40 mmol, 3 eq) and Et$_3$N (0.39 mL, 2.80 mmol, 1.0 eq) were added to a solution of 4-amino-3-iodobenzonitrile (0.68 g, 2.8 mmol) in MeCN (15 mL) and MeOH (7.5 mL). The reaction mixture was purged with N$_2$, the flask was capped, and a balloon containing CO was attached. After bubbling CO gas into the solution through a needle attached to the balloon for 5 min, the mixture was heated under a CO balloon at 60° C. overnight. The mixture was diluted with EtOAc (200 mL) and filtered. The filtrate was washed with water (3×40 mL), brine (1×), dried (Na$_2$SO$_4$) and filtered. Solvent was evaporated in vacuo. The residue was purified by flash chromatography on silica gel to provide methyl 2-amino-5-cyanobenzoate (0.268 g, 54%) as a white solid. $^1$H NMR (400 MHz, Chloroform-d) δ 8.17 (d, J=2.0 Hz, 1H), 7.43 (dd, J=8.7, 2.1 Hz, 1H), 6.67 (d, J=8.6 Hz, 1H), 6.33 (s, 2H), 3.88 (s, 3H).

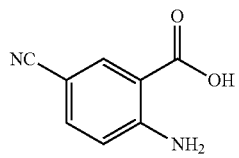 [SMILES: N#Cc1ccc(N)c(C(=O)O)c1]

2-amino-5-cyanobenzoic acid

To a solution of methyl 2-amino-5-cyanobenzoate (0.120 g, 0.68 mmol) in THF (3.5 ml), was added a solution of lithium hydroxide (0.033 g, 1.36 mol, 2.0 eq) in H$_2$O (3.5 ml). After stirring at rt for 3 h, the reaction mixture was concentrated. The residue was diluted with H$_2$O (5 ml) and acidified to pH~3 using 1M HCl. The precipitate was collected by filtration, washed with H$_2$O and dried under air. 2-amino-5-cyanobenzoic acid (0.11 g, 95%) was obtained as a white solid. $^1$H NMR (400 MHz, DMSO-d$_6$) δ 8.04 (d, J=2.1 Hz, 1H), 7.70-7.33 (m, 3H), 6.86 (d, J=8.8 Hz, 1H).

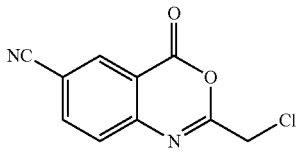 [SMILES: N#Cc1ccc2nc(CCl)oc(=O)c2c1]

2-(chloromethyl)-4-oxo-4H-benzo[d][1,3]oxazine-6-carbonitrile

To a solution of 2-amino-5-cyanobenzoic acid (0.10 g, 0.617 mmol, 1 eq) in CH$_2$Cl$_2$ (1.0 mL) was added triethylamine (0.3 mL, 2.15 mmol, 3.5 eq), and then the mixture was cooled to 0° C. in an ice bath, and a solution of chloroacetyl chloride (0.16 mL, 2.0 mmol, 3.3 eq) in CH$_2$Cl$_2$ (1.5 mL) was slowly added. The reaction mixture was stirred at rt for 16 h. The solvent was removed in vacuo and water was added to the remaining solid. The solid was filtered, rinsed with water (10 mL) and dried under air to afford 2-(chloromethyl)-4-oxo-4H-benzo[d][1,3]oxazine-6-carbonitrile: (0.15 g, 99%) as a yellow solid. The product was used in the following step without further purification. $^1$H NMR (400 MHz, DMSO-d$_6$) δ 12.08 (s, 1H), 8.70 (d, J=8.8 Hz, 1H), 8.39 (d, J=2.1 Hz, 1H), 8.09 (dd, J=8.8, 2.1 Hz, 1H), 4.53 (s, 2H).

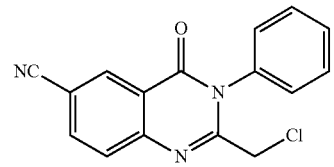 [SMILES: N#Cc1ccc2nc(CCl)n(-c3ccccc3)c(=O)c2c1]

2-(chloromethyl)-4-oxo-3-phenyl-3,4-dihydroquinazoline-6-carbonitrile

To a microwave vial containing a solution of 2-(chloromethyl)-4-oxo-4H-benzo[d][1,3]oxazine-6-carbonitrile (0.14 g, 0.59 mmol, 1 eq) in CH$_2$Cl$_2$ (0.8 mL) was added phosphorus oxychloride (0.11 mL, 1.17 mmol, 2 eq) and a solution of aniline (0.07 mL, 0.76 mmol, 1.3 eq) in CH$_2$Cl$_2$ (0.8 mL). The resulting mixture was heated in a MW reactor at 150° C. for 15 min. The reaction mixture was slowly quenched with saturated NaHCO$_3$ (3 mL). The precipitate was filtered, rinsed with water (8 mL) and dried under air to afford 2-(chloromethyl)-4-oxo-3-phenyl-3,4-dihydroquinazoline-6-carbonitrile (0.138 g, 80%) as a burnt-orange solid. $^1$H NMR (400 MHz, Chloroform-d) δ 8.63 (dd, J=2.0, 0.6 Hz, 1H), 8.03 (dd, J=8.5, 1.9 Hz, 1H), 7.89 (dd, J=8.5, 0.6 Hz, 1H), 7.69-7.58 (m, 3H), 7.41-7.35 (m, 2H), 4.30 (s, 2H).

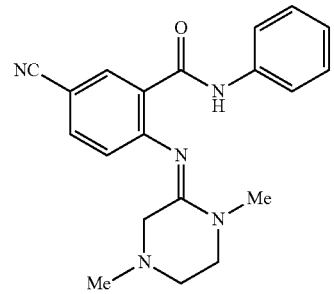 [SMILES: CN1CCN(C)/C(=N/c2ccc(C#N)cc2C(=O)Nc2ccccc2)C1]

(E)-5-cyano-2-((1,4-dimethylpiperazin-2-ylidene) amino)-N-phenylbenzamide

To a solution of 2-(chloromethyl)-4-oxo-3-phenyl-3,4-dihydroquinazoline-6-carbonitrile (0.030 g, 0.10 mmol, 1 eq) in DMF (2 ml), was added K$_2$CO$_3$ (0.028 g, 0.20 mmol, 2.0 eq) and N,N'-dimethylethanediamine (0.009 g, 0.10 mmol, 1.0 eq). After stirring for 1.5 h, the reaction mixture was purified by chromatography to afford (E)-5-cyano-2-((1,4-dimethylpiperazin-2-ylidene)amino)-N-phenylbenzamide (0.007 g, 20%) as a light yellow solid. Mp: 167-169° C. $^1$H NMR (400 MHz, Chloroform-d) δ 10.95 (s, 1H), 8.61 (d, J=2.1 Hz, 1H), 7.68-7.62 (m, 2H), 7.59 (dd, J=8.2, 2.1 Hz, 1H), 7.42-7.35 (m, 2H), 7.15 (tt, J=8.0, 2.1 Hz, 1H), 6.81 (d, J=8.3 Hz, 1H), 3.47 (d, J=4.1 Hz, 2H), 3.29 (s, 3H), 3.12 (s, 2H), 2.69 (d, J=4.1 Hz, 2H), 2.28 (s, 3H). $^{13}$C NMR (101 MHz, CDCl$_3$) δ 162.86, 156.28, 152.07, 138.24, 136.09, 134.50, 129.10, 126.64, 124.18, 124.09, 120.24, 118.95, 105.83, 55.07, 51.90, 49.65, 45.32, 36.81. LCMS purity:

99.5%. LCMS retention time: 3.106 min. HRMS m/z calculated for $C_{20}H_{21}N_5O$ [M$^+$+H]: 348.1746. found 348.1820.

Synthesis of (E)-2-((1-ethyl-4-methylpiperazin-2-ylidene)amino)-5-nitro-N-phenylbenzamide

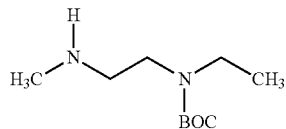

tert-Butyl ethyl(2-(methylamino)ethyl)carbamate (2-aminoethyl)ethylcarbamic acid tert-butyl ester (ChemImpex, 377 mg, 2.00 mmol, 1 eq) was dissolved in toluene (5 mL), and then benzaldehyde (0.26 mL, 2.56 mmol, 1.3 eq) was added dropwise at rt. The reaction flask was equipped with a Dean-Stark trap and a reflux condenser. The mixture was heated at 150° C. for 1.5 hours. After cooling to rt, the Dean-Stark trap was removed and a solution of methyl p-toluenesulfonate (0.31 mL, 2.05 mmol, 1.03 eq) in toluene (0.5 mL) was added dropwise. The mixture was heated to gentle reflux at 125° C. for 15 hours. After cooling to rt, water (2 mL) was added and the mixture was heated at 80° C. for 30 min. After cooling to rt, the biphasic layers were separated and 2 M aq. KOH (4 mL) was added to the aq. layer. The product was extracted from the aq. layer with $CH_2Cl_2$ (3×15 mL) and dried with $Na_2SO_4$ to give tert-butyl ethyl(2-(methylamino)ethyl)carbamate (171 mg, 42%) as a clear, pale yellow oil, which was used in the next step without further purification.

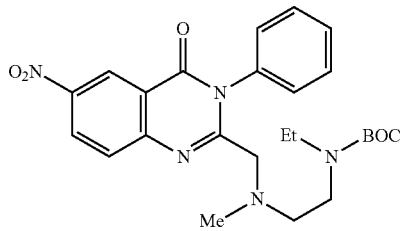 [SMILES: CCN(CCN(C)Cc1nc2ccc([N+](=O)[O-])cc2c(=O)n1-c1ccccc1)C(=O)OC(C)(C)C]

tert-Butyl ethyl(2-(methyl((6-nitro-4-oxo-3-phenyl-3,4-dihydroquinazolin-2-yl)methyl)amino)ethyl)carbamate Using a MW vial, 2-(chloromethyl)-6-nitro-3-phenylquinazolin-4(3H)-one (177 mg, 0.56 mmol, 1 eq) was dissolved in MeCN (2.6 mL). Potassium carbonate (157 mg, 1.14 mmol, 2 eq), tert-butyl ethyl(2-(methylamino)ethyl)carbamate (161 mg, 0.80 mmol, 1.4 eq), and potassium iodide (36 mg, 0.22 mmol, 0.4 eq) were added successively to the reaction vial. The mixture was heated in a MW reactor at 80° C. for 10 min. The product was purified by flash chromatography (CombiFlash, 12 g silica, 0-10% MeOH/$CH_2Cl_2$) to give tert-butyl ethyl(2-(methyl((6-nitro-4-oxo-3-phenyl-3,4-dihydroquinazolin-2-yl)methyl)amino)ethyl)carbamate (88 mg, 33%) as a clear, dark red oil. $^1$H NMR (400 MHz, CDCl$_3$) δ 9.07 (d, J=2.7 Hz, 1H), 8.53 (dd, J=8.9, 2.6 Hz, 1H), 7.88 (d, J=8.9 Hz, 1H), 7.59-7.52 (m, 3H), 7.33-7.29 (m, 2H), 3.37 (s, 2H), 3.20-3.00 (m, 4H), 2.52-2.42 (m, 2H), 2.22 (s, 3H), 1.40 (br s, 9H), 1.02 (t, J=7.2 Hz, 3H).

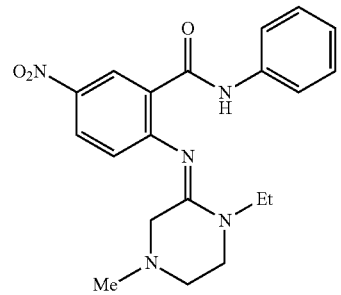 [SMILES: CCN1CCN(C)C/C1=N\c1ccc([N+](=O)[O-])cc1C(=O)Nc1ccccc1]

(E)-2-((1-ethyl-4-methylpiperazin-2-ylidene)amino)-5-nitro-N-phenylbenzamide

To a solution of tert-butyl ethyl(2-(methyl((6-nitro-4-oxo-3-phenyl-3,4-dihydroquinazolin-2-yl)methyl)amino)ethyl)carbamate (88 mg, 0.183 mmol) in $CH_2Cl_2$ (2.8 mL) was added TFA (1.2 mL, 15.67 mmol). The reaction was stirred at rt for 45 min. After the reaction was complete, water (7 mL) and $CH_2Cl_2$ (7 mL) were added and the reaction mixture was adjusted to pH 10 using saturated aq. $Na_2CO_3$ (5 mL). The product was extracted with $CH_2Cl_2$ (3×15 mL) and purified by flash chromatography (CombiFlash, 0-5% MeOH/$CH_2Cl_2$) to give (E)-2-((1-ethyl-4-methylpiperazin-2-ylidene)amino)-5-nitro-N-phenylbenzamide (18 mg, 23%) as a pale, yellow solid. $^1$H NMR (400 MHz, CDCl$_3$) δ 10.66 (s, 1H), 9.14 (d, J=2.8 Hz, 1H), 8.16 (dd, J=8.8, 2.8 Hz, 1H), 7.65-7.56 (m, 2H), 7.38-7.33 (m, 2H), 7.16-7.10 (m, 1H), 6.81 (d, J=8.8 Hz, 1H), 3.78 (q, J=7.1 Hz, 2H), 3.46 (t, J=5.6 Hz, 2H), 3.12 (s, 2H), 2.68 (t, J=5.6 Hz, 2H), 2.25 (s, 3H), 1.30 (t, J=7.2 Hz, 3H). $^{13}$C NMR (101 MHz, CDCl$_3$) δ 162.92, 155.87, 154.58, 142.87, 138.20, 129.17, 127.84, 126.57, 126.08, 124.47, 123.98, 120.68, 55.39, 51.99, 46.78, 45.33, 43.56, 12.16. LCMS retention time: 3.344 min, purity at 214 nm=88%. FIRMS m/z calculated for $C_{20}H_{24}N_5O_3$ [M$^+$+H] 382.1879. found 382.1915. Pale yellow solid, mp 150-157° C. (decomposition).

Synthesis of 6-nitro-3-phenyl-2-(piperazin-1-ylmethyl)quinazolin-4(3H)-one

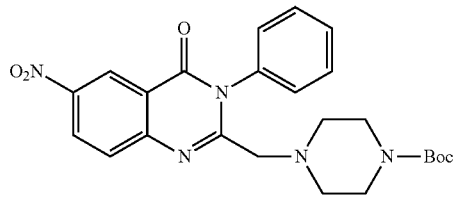 [SMILES: CC(C)(C)OC(=O)N1CCN(Cc2nc3ccc([N+](=O)[O-])cc3c(=O)n2-c2ccccc2)CC1]

tert-Butyl 4-((6-nitro-4-oxo-3-phenyl-3,4-dihydroquinazolin-2-yl)methyl)piperazine-1-carboxylate. 2-(chloromethyl)-6-nitro-3-phenylquinazolin-4(3H)-one (253 mg, 0.801 mmol, 1 eq) was dissolved in $CH_2Cl_2$ (3.6 mL). Potassium carbonate (224 mg, 1.621 mmol, 2 eq), 1-piperazinecarboxylic acid, 1,1-dimethylethyl ester (224 mg, 1.203 mmol, 1.5 eq), and potassium iodide (50 mg, 0.301 mmol, 0.4 eq) were added successively to the reaction vial. The mixture was heated in a MW reactor at 80° C. for 5 min. The product was purified by flash chromatography (CombiFlash, 0-50% EtOAc/hexanes) to give tert-butyl 4-((6-nitro-4-oxo-3-phenyl-3,4-dihydroquinazolin-2-yl)methyl)piperazine-1-carboxylate (103 mg, 28%) as a white solid. $^1$H NMR (400 MHz, CDCl$_3$) δ 9.13 (d, J=2.5 Hz, 1H), 8.56 (dd, J=9.0, 2.7 Hz, 1H), 7.87 (d, J=8.9 Hz, 1H), 7.60-7.51 (m, 3H), 7.35-7.29 (m, 2H), 3.33-3.27 (m, 6H), 2.27 (t, J=4.8 Hz, 4H), 1.43 (s, 9H).

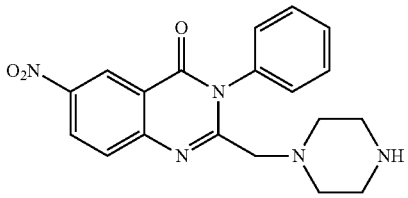 [SMILES: O=c1c2cc([N+](=O)[O-])ccc2nc(CN2CCNCC2)n1-c1ccccc1]

6-nitro-3-phenyl-2-(piperazin-1-ylmethyl)quinazolin-4(3H)-one tert-butyl 4-((6-nitro-4-oxo-3-phenyl-3,4-dihydroquinazolin-2-yl)methyl)piperazine-1-carboxylate (73 mg, 0.157 mmol) was dissolved in CH$_2$Cl$_2$ (2.4 mL) and then TFA (1 mL, 13.06 mmol) was added dropwise. The mixture was stirred at rt for 2 h. After the reaction was complete, water (6 mL) and CH$_2$Cl$_2$ (6 mL) were added, and the reaction mixture was adjusted to pH 10 using saturated aq. Na$_2$CO$_3$ (4 mL). The product was extracted with CH$_2$Cl$_2$ (3×12 mL) and purified by flash chromatography (CombiFlash, 0-10% MeOH/DCM) to give 6-nitro-3-phenyl-2-(piperazin-1-ylmethyl)quinazolin-4(3H)-one (49 mg, 85%) as a white solid. $^1$H NMR (400 MHz, DMSO-d$_6$) δ 8.82 (d, J=2.5 Hz, 1H), 8.61 (dd, J=9.0, 2.7 Hz, 1H), 7.93 (d, J=9.0 Hz, 1H), 7.58-7.49 (m, 5H), 3.25 (s, 2H), 2.66 (t, J=4.5 Hz, 4H), 2.19 (t, J=4.7 Hz, 4H). LCMS retention time: 2.607 min, purity at 214 nm=99.2%. HRMS m/z calculated for C$_{19}$H$_{20}$N$_5$O$_3$ [M$^+$+H] 366.1561. found 366.1567. White solid, mp 190-195° C.

Synthesis of (E)-2-((1,4-dimethylpiperazin-2-ylidene)amino)-N-(3-fluorophenyl)-5-nitrobenzamide

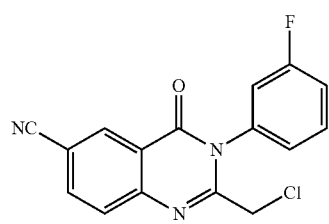 [SMILES: N#Cc1ccc2nc(CCl)n(-c3cccc(F)c3)c(=O)c2c1]

2-(chloromethyl)-3-(3-fluorophenyl)-4-oxo-3,4-dihydroquinazoline-6-carbonitrile. To a microwave vial containing 2-(chloromethyl)-4-oxo-4H-benzo[d][1,3]oxazine-6-carbonitrile (0.147 g, 0.616 mmol, 1 eq) was added CH$_2$Cl$_2$ (0.7 mL). Phosphorus oxychloride (0.12 mL, 1.23 mmol, 2.0 eq) and a solution of 3-fluoroaniline (0.08 mL, 0.80 mmol, 1.3 eq) in CH$_2$Cl$_2$ (1.0 mL) was added and the mixture was heated in a MW reactor at 150° C. for 15 min. The reaction mixture was slowly quenched with saturated NaHCO$_3$ (5 mL). The precipitate was filtered, rinsed with water (8 mL) and dried under air to afford 2-(chloromethyl)-3-(3-fluorophenyl)-4-oxo-3,4-dihydroquinazoline-6-carbonitrile (0.150 g, 78%) as a burnt-orange solid. $^1$H NMR (400 MHz, Chloroform-d) δ 8.60 (d, J=2.0 Hz, 1H), 8.01 (dd, J=8.5, 2.0 Hz, 1H), 7.87 (d, J=8.5 Hz, 1H), 7.59 (td, J=8.2, 5.9 Hz, 1H), 7.32 (tdd, J=8.3, 2.5, 1.0 Hz, 1H), 7.17 (ddd, J=8.0, 2.1, 1.0 Hz, 1H), 7.13 (dt, J=8.6, 2.3 Hz, 1H), 4.29 (s, 2H).

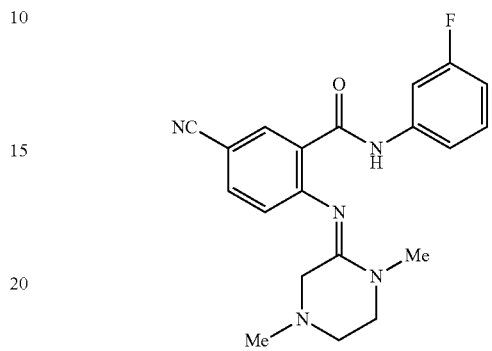

(E)-2-((1,4-dimethylpiperazin-2-ylidene)amino)-N-(3-fluorophenyl)-5-nitrobenzamide To a solution of 2-(chloromethyl)-3-(3-fluorophenyl)-4-oxo-3,4-dihydroquinazoline-6-carbonitrile (0.020 g, 0.064 mmol, 1.0 eq) in DMF (0.64 ml), was added K$_2$CO$_3$ (0.018 g, 0.128 mmol, 2.0 eq) and N,N'-dimethylethanediamine (0.007 g, 0.083 mmol, 1.3 eq). After stirring for 2 h, the reaction mixture was purified by chromatography to afford (E)-2-((1,4-dimethylpiperazin-2-ylidene)amino)-N-(3-fluorophenyl)-5-nitrobenzamide (0.010 g, 43%) as a light yellow solid. Mp: 179-182° C. $^1$H NMR (400 MHz, Chloroform-d) δ 11.09 (s, 1H), 8.59 (d, J=2.1 Hz, 1H), 7.63-7.55 (m, 2H), 7.35-7.24 (m, 2H), 6.89-6.79 (m, 2H), 3.48 (t, J=4.1 Hz, 2H), 3.29 (s, 3H), 3.13 (s, 2H), 2.71 (t, J=4.1 Hz, 2H), 2.29 (s, 3H). $^{13}$C NMR (101 MHz, CDCl$_3$) δ 164.30, 163.01, 161.87, 156.49, 152.01, 139.84, 139.73, 136.11, 134.67, 130.13, 130.04, 126.29, 124.13, 118.84, 115.39, 110.95, 110.74, 107.82, 107.56, 55.12, 51.89, 49.68, 45.33, 36.84. Purity: 99.3%. LCMS retention time: 3.210 min. HRMS m/z calculated for C$_{20}$H$_{20}$FN$_5$O [M$^+$+H]: 366.1653. found 366.1727.

Assay Conditions

HTS Primary and Confirmatory Assay Using TC-83.

Cell Culture: Vero 76 cells obtained from ATCC (CRL-1587) were cultured and maintained in MEM-E (Invitrogen, 10370-088) with 10% Hi-FBS (Invitrogen 16000), 1% Penicillin/Streptomycin/L-glutamine (Invitrogen 10378-024) and 1% HEPES (Invitrogen 15630-080). The cells are maintained at 37° C., 5.0% CO$_2$ to 100% confluence being passaged 1:4 every 3-4 days. For cell plating, cells were detached from flask bottom by using Trypsin-EDTA solution and then re-suspended in a growth media. Cells were passaged no more than ten times after being thawed.

VEEV culture: VEEV TC-83 was used for screening. The VEEV stock was prepared in Vero76 cells using an initial stock obtained from Dr. Chung.

Compound Dosing/Plating: The positive control was MPA at 10 uM final well concentration. The compounds were diluted in complete growth medium to 6× concentrated dosing solution which was dispensed into 384-well black clear-bottom tissue culture treated plates (5 μL volume).

Single Dose Compound Preparation: The MLSMR library was plated at 25 single dose concentration.

Dose Response Compound Preparation: The compounds were tested in a dose response format using a 1:2 serial dilution with the highest concentrations starting at 25 µm and extending to 0.05 µM over a 10-plate 1:2 serial dilution pattern. DMSO and compounds were diluted in assay media to 6× and 5 µL was dispensed to assay plates. The final DMSO in the assay for all screening concentrations was 0.25%.

Virus Addition: VEEV stock was diluted in the culture media to 6.44 pfu/ml. (MOI 4e-5)

VEEV and Cell Plating: 3,000 cells/well alone or with VEEV virus at the previously indicated dilution (180,000 cells/ml) were plated in 25 uL using a Matrix WellMate. All additions were done using a Matrix WellMate housed in a class II Biosafety Cabinet within the BSL-2 laboratory. The plates were incubated in an actively humidified incubator with 5.0% $CO_2$ at 37° C. for 72 h and 95% humidity.

Endpoint Read: The assay plates were equilibrated to room temperature for 30 minutes and then an equal volume of CellTiter-Glo reagent (Promega Inc.) was added to each well. Plates were incubated for 10 min at room temperature and luminescence was measured using a Perkin Elmer Envision multi-label reader.

Cell-Based Confirmatory Screen for Compounds that Inhibit VEEV, TC-83.

Cell Culture: Vero 76 (CRL-1587, ATCC) were purchased from ATCC and maintained in 37° C. incubator with 5% $CO_2$. The cells were cultured in a complete media (Minimum Essential Media with Earle's salt and 10% fetal bovine serum). Cells were passaged once a week and harvested from flasks using 0.05% trypsin-EDTA.

Assay Media—Preparation of Complete DMEM media: 5 mL Pen/Strep (Gibco, Cat. No. 15149) and 50 mL of heat-inactivated FBS (Gibco, Cat. No. 10082147) was added to 500 mL of Dulbecco's Modified Eagle Medium (Gibco, Cat. No. 11995-073).

Virus: TC-83 strain was obtained from Dr. Brett Beitzel from United State Army Research Medical Research Institute for Infectious diseases and amplified in BHK C-21 cell line once.

Dose Response Compound Preparation: For dose response screening, compounds or carrier control (DMSO) were diluted to 3× in Complete DMEM media. Test compounds were serially diluted 1:2 resulting in an 8 point dose response dilution series. (final plate well concentration ranging from 50 uM to 0.39 µM and a final DMSO concentration of 0.25%). 30 µl of each dilution was dispensed to assay plates (0.75% DMSO) in duplicate.

Control Drug: The positive control drug for this assay, mycophenolic acid was solubilized in DMSO. It was diluted and added to the assay plates as described for test compounds. Final concentration for ribavirin was 10 µM. All wells contained 0.25% DMSO.

Assay Set up: Vero 76 cells were plated in 96-well plates at a density of 15,000 cells per well in a volume of 45 µL of DMEM complete media. The cells were grown for 24 hours prior to testing in a 5% $CO_2$, 37 C cell culture incubator. Viruses, TC-83 strain, was diluted in cell culture medium to be 750 pfu/15 uL (0.05 MOI) and then added to the plates at a volume of 15 µL per well. The plates were incubated for 48 hours in a 37° C. incubator with 5% $CO_2$.

Endpoint Read: Following the two day incubation period, the assay plates were equilibrated to room temperature for 10 min and an equal volume (90 µL) of Cell Titer-Glo reagent (Promega Inc.) was added to each well using a Microflow (Biotek, VT) and plates were incubated for an additional 10 min at room temperature. At the end of the incubation, luminescence was measured using a Synergy4 Multimode plate reader (Biotek, VT) with an integration time of 0.2 s.

Data Analysis: Results are reported as percent (%) CPE inhibition and were calculated using the following formula: % CPE inhibition=100*(Test Cmpd−Med Virus)/(Med Cells−Med Virus). Four ribavirin positive control wells were included on each plate for quality control purposes. To quantify the viral cytopathic effect, IC50s were calculated for each substance using the 4 parameter Levenburg-Marquardt algorithm with the minimum and maximum parameters locked at 0 and 100, respectively.

Cell-Based Confirmatory Screen for Compounds that Inhibit VEEV, V3526.

Cell Culture: Vero 76 (CRL-1587, ATCC) were purchased from ATCC and maintained in 37° C. incubator with 5% $CO_2$. The cells were cultured in a complete media (Minimum Essential Media with Earle's salt and 10% fetal bovine serum). Cells were passaged once a week and harvested from flasks using 0.05% trypsin-EDTA.

Assay Media—Preparation of Complete DMEM media: 5 mL Pen/Strep (Gibco, Cat. No. 15149) and 50 mL of heat-inactivated FBS (Gibco, Cat. No. 10082147) was added to 500 mL of Dulbecco's Modified Eagle Medium (Gibco, Cat. No. 11995-073).

Virus: V3526 strain. Virus was rescued from BHK C-21 cells that were transfected with infectious V3526 RNA. The rescued virus was amplified in BHK C-21 cells once and then used as a stock virus.

Dose Response Compound Preparation: For dose response screening, compounds or carrier control (DMSO) were diluted to 3× in Complete DMEM media. Test compounds were serially diluted 1:2 resulting in an 8 point dose response dilution series. (final plate well concentration ranging from 50 µM to 0.39 µM and a final DMSO concentration of 0.25%). 30 µL of each dilution was dispensed to assay plates (0.75% DMSO) in duplicate.

Control Drug: The positive control drug for this assay, mycophenolic acid was solubilized in DMSO. It was diluted and added to the assay plates as described for test compounds. Final concentration for ribavirin was 10 µM. All wells contained 0.25% DMSO.

Assay Set up: Vero 76 cells were plated in 96-well plates at a density of 15,000 cells per well in a volume of 45 µL of DMEM complete media. The cells were grown for 24 hours prior to testing in a 5% $CO_2$, 37° C. cell culture incubator. V3526 VEEV virus, was diluted in cell culture medium to be 750 pfu/15 uL (0.05 MOI) and then added to the plates at a volume of 15 µL per well. The plates were incubated for 48 hours in a 37° C. incubator with 5% $CO_2$.

Endpoint Read: Following the two day incubation period, the assay plates were equilibrated to room temperature for 10 min and an equal volume (90 µL) of Cell Titer-Glo reagent (Promega Inc.) was added to each well using a Microflow (Biotek, VT) and plates were incubated for an additional 10 min at room temperature. At the end of the incubation, luminescence was measured using a Synergy4 Multimode plate reader (Biotek, VT) with an integration time of 0.2 s.

Cell-Based Secondary Assay for Compounds that Inhibit VEEV, TC-83 and other Alphaviruses (Trinidad Donkey).

Biosafety and Biosecurity: All experiments with VEEV Trinidad donkey (TrD) strain was done in the Regional Biocontainment Laboratory (RBL) in University of Louisville. All procedures were done in compliance with Select Agent Rules.

Cell Culture: Vero 76 cells obtained from ATCC (CRL-1586) were cultured and maintained in in Dulbecco's Modified Eagle's Medium (DMEM) with 4500 mg/L glucose, 2 mM L-glutamine, and 10% FBS (culture media). The cells are maintained at 37° C., 5.0% $CO_2$ to 100% confluence being passaged every three to seven days. For cell plating, cells were detached from flask bottom by using 0.05% Trypsin-EDTA solution and then re-suspended in a growth media.

VEEV culture: VEEV TrD strain was used for screening. The VEEV TrD stock was prepared in Vero 76 cells using an initial stock obtained from World Reference Center for Emerging Viruses and Arboviruses (Dr. Robert Tesh). Briefly, cells were grown in two T-175 flasks to 50% confluence in a culture media. The cells were infected with 1 mL of diluted virus stock (1:10 dilution of the original stock) per T175 for 1.5 hours and then washed, and replenished with 25 mL media. The cells were incubated for 2 days in an incubator at 37° C., 5% $CO_2$ and high humidity. The supernatant was harvested and the cell debris pelleted by centrifuging at 1,000 rpm for 5 minutes at 18° C. The supernatant was aliquoted (1 mL per tube) and stored at −80° C. These virus stocks were titrated in Vero 76 cells using an agarose overlay plaque method and the titers were 2.0×E10 pfu/mL.

Dose Response Compound Preparation: The compounds were tested in a dose response format using a 1:2 serial dilution with the highest concentrations starting at 12.5 µM and extending to 0.09 µM over 8 points 1:2 serial dilution pattern. DMSO and compounds were diluted in assay media to 3× and 30 µL was dispensed to assay plates (see below). The final DMSO in the assay for all screening concentrations was 0.25%.

Assay Set up: 45 µl of Vero 76 cell suspension (267,000 cells/mL) were plated in clear bottom black well 96-well plates and the plates were incubated in an incubator at 37° C. in a humidified 5% $CO_2$ atmosphere. The next day, thirty uL of drugging media (0.75% DMSO) were added to the each wells and the plates were incubated at 37° C. for an hour. The plates were transferred into a BSL-3 lab in the RBL. Each well received fifteen µL of VEEV TrD virus diluted in Complete media (40,000 pfu/mL, final 0.05 MOI). For the cell control wells, Complete media were added instead of virus solution. Drug plating was conducted using a EV0100, 96MAC (Tecan) and virus solution was added using MicroFlo (Biotek). The assay plates were incubated for two days at 37° C., 5% $CO_2$ and 90% relative humidity.

Endpoint Read: The assay plates were equilibrated to room temperature for 30 minutes and then an equal volume of CellTiter-Glo reagent (Promega Inc.) was added to each well. Plates were incubated for 10 min at room temperature and luminescence was measured using a Synergy4 HT multi-label reader.

Vero76 Cytotoxicity Assay for VEEV Compounds

Cell Culture: Vero 76 cells obtained from ATCC (CRL-1587) were cultured and maintained in MEM-E (Invitrogen, 10370-088) with 10% Hi-FBS (Invitrogen 16000), 1% Penicillin/Streptomycin/L-glutamine (Invitrogen 10378-024) and 1% HEPES (Invitrogen 15630-080). The cells are maintained at 37° C., 5.0% $CO_2$ to 100% confluence being passaged 1:4 every 3-4 days. For cell plating, cells were detached from flask bottom by using Trypsin-EDTA solution and then re-suspended in a growth media. Cells were passaged no more than ten times after being thawed.

Compound Dosing/Plating: Carrier control/compounds were diluted in complete growth medium to prepare a 6× concentrated dosing solution which was dispensed into 384-well black clear-bottom tissue culture treated plates (5 µL volume).

Cell Plating: Twenty-five uL of complete growth medium containing 3000 cells were dispensed per well. Plates were incubated at 37° C., 5% $CO_2$ for 72 h prior to endpoint detection.

Endpoint/Detection: At the end of the treatment period, assay plates were removed from the incubator and equilibrated to room temperature for 10 min. Thirty uL of Cell Titer Glo reagent was added and plates were incubated for an additional 10 min in the dark. At the end of the incubation, assay plates were analyzed using a PerkinElmer Envision microplate reader in luminescence mode with an integration time of 0.1 s.

Virus Titer Reduction Secondary Screen for Compounds that Inhibit VEEV (Strain Trinidad Donkey)

Biosafety and Biosecurity: All experiments with VEEV Trinidad donkey strain was done in the Regional Biocontainment Laboratory in University of Louisville. All procedures were done in compliance with Select Agent Rules.

Cell Culture: Vero 76 cells (ATCC; CRL1586) were cultured in Dulbecco's Modified Eagle's Medium (DMEM) with 4500 mg/L glucose, 2 mM L-glutamine, and 10% FBS (culture media). The cells are maintained at 37° C., 5.0% $CO_2$ to 100% confluence being passaged every three to seven days. For cell plating, cells were detached from flask bottom by using 0.05% Trypsin-EDTA solution and then re-suspended in a growth media.

VEEV culture: Trinidad Donkey (TrD) was used for screening. The VEEV TrD stock was prepared in Vero 76 cells using an initial stock obtained from World Reference Center for Emerging Viruses and Arboviruses (Dr. Robert Tesh). Briefly, cells were grown in two T-175 flasks to 50% confluence in a culture media. The cells were infected with 1 mL of diluted virus stock (1:10 dilution of the original stock) per T175 for 1.5 hours and then washed, and replenished with 25 mL media. The cells were incubated for 2 days in an incubator at 37° C., 5% $CO_2$ and high humidity. The supernatant was harvested and the cell debris pelleted by centrifuging at 1,000 rpm for 5 minutes at 18° C. The supernatant was aliquoted (1 ml per tube) and stored at −80° C. These virus stocks were titrated in Vero 76 cells using an agarose overlay plaque method and the titer was 2.0×E10 pfu/ml.

Cell Plating: Vero 76 cells were seeded at 70% confluence in a 12-well plate in a volume of 1 mL and incubated for overnight at 37° C. with 5% $CO_2$ and high humidity.

Virus Addition: The cells were infected with virus by adsorption for an hour. Cell culture media in the 12-well plates were removed completely and the cells were infected with either mock virus (media only) or VEEV. VEEV stock was diluted in the culture media to 9×E03 pfu/ml and 200 µL was added to the test wells and the virus control wells (final MOI of 0.1). The plates were incubated in an actively humidified incubator with 5.0% $CO_2$ at 37° C. for one hour. During the incubation, plates were gently rocked every 20 min. to ensure the coverage of the cells with virus. After the adsorption, the cells were rinsed 1 mL of PBS per well and then replenished with the media containing testing articles. All additions were performed in a class II Biosafety Cabinet. The plates were incubated in an actively humidified incubator with 5.0% $CO_2$ at 37° C. for 48 h.

Control and Drug Preparation: Carrier Control consisted of DMSO diluted in assay media to 0.25% and 1000 µL was dispensed to both cell and virus control wells of 12-well tissue culture treated plates. Test compounds were diluted in media to be at target concentration with a DMSO concentration of 0.25%.

Titration of Progeny viruses (Mini plaque assay): Titer of progeny viruses produced from the cell was measured by a mini plaque assay in 96-well plate format. Fresh Vero 76 cells were seeded and grown in 96-well plates overnight. The cell culture supernatants from the 96-well plates were emptied and the cells were infected with 25 μL of 10-fold serial dilutions of progeny virus containing medium from respective samples (drug treated or untreated). The plates were incubated for one hour in an incubator at 37° C., 5% $CO_2$. The cells were rinsed with 100 μL per well of PBS once and then replenished with DMEM with 0.75% methylcellulose and 10% FBS. The cell plates were incubated at 37° C., 5% $CO_2$, and high humidity for an additional three days. Crystal violet solution with 4% paraformaldehyde was used to developed plaques in the wells. The assay plates were equilibrated to room temperature for 10 minutes and then an equal volume of the crystal violet solution was added to each well. The plates were incubated for 60 min at room temperature and stained one more time. After a wash the plates with water, the number of plaques in each wells were determined by a visual counting. Virus titers were calculated by: No. of plaques×10E (dilution fold at the counting)*1000/25 (pfu/mL). Compounds treatment were done in a duplicate independently and mean from duplicates of titration was used. Log reduction of titer was calculated by: $Log_{10}$(titer of Pos control)−$Log_{10}$) (titer of sample).

Counter Screen of Venezuelan Equine Encephalitis Virus (VEEV) Inhibitors in a Cell-Based Anti-Respiratory Syncytial Virus (RSV) Assay Cell Culture: HEp-2 cells (ATCC CCL-23, American Tissue Culture Type) were maintained as adherent cell lines in DMEM with 2 mM L-glutamine and 10% fetal bovine serum (FBS) at 37° C. in a humidified 5% $CO_2$ atmosphere. Cells were passaged as needed and harvested from flasks using 0.05% trypsin-EDTA.

Assay Media—Preparation of Complete DMEM/F12: DMEM/F12 (Invitrogen, Cat. No. 11320) was supplemented with 5 mL of Pen/Strep (Invitrogen, Cat. No. 10378016), 5 mL of 200 mM glutamine (Invitrogen, Cat No. 25030-081), and 10 mL of HI-FBS was added per 500 mL of media.

RSV culture: Human respiratory syncytial virus (HRSV) strain Long (ATCC VR-26) was used for screening. The RSV stock was prepared in HEp-2 cells using an initial stock obtained from ATCC. Briefly, HEp-2 cells were grown in two T-175 flasks to 50% confluence in Dulbecco's Modified Eagle Medium: Nutrient Mixture F-12 (DMEM/F12), pH 7.5 with 2.5 mM L-glutamine, 2% FBS and 125 U of penicillin, 125 ug of streptomycin per ml. 0.2 mL of RSV was added to 25 ml of CDMEM/F12. After three days incubation at 37° C., 5% $CO_2$ and high humidity, the supernatant was harvested and the cell debris pelleted by centrifuging at 1,000 rpm for 5 minutes at 18° C. Trehalose and FBS were added to a final concentration of 10% each and the supernatant was aliquoted (1 ml per tube) and stored at −80° C. These virus stocks were titrated in HEp-2 cells using an agarose overlay plaque method and the titer was 1.0 E7 pfu/ml.

Dose Response Compound Preparation: For dose response screening, compounds or carrier control (DMSO) were diluted to 3× in Complete DMEM/F12. Test compounds were serially diluted 1:2 resulting in an 8 point dose response dilution series. (final plate well concentration ranging from 50 μM to 0.39 μM and a final DMSO concentration of 0.25%). 39 μL of each dilution was dispensed to assay plates (0.75% DMSO) in triplicate.

Control Drug: The positive control drug for this assay, MPA was solubilized in DMSO.

Preparation of HEp-2 cells: Cells were harvested and resuspended to 267,000 cells per ml in Complete DMEM/F12.

Assay Set up: Forty five ul of HEp-2 cell suspension (12,000 cells/well) were plated in clear bottom black well 96-well plates and the plates were incubated in an incubator at 37° C. in a humidified 5% $CO_2$ atmosphere. The next day, 30 μL of drugging media (0.75% DMSO) were added to the each wells and the plates were incubated at 37° C. for an hour. Each well received 15 μL of RSV diluted in Complete DMEM/F12 media (40,000 pfu/mL, final 0.05 MOI). For the cell control wells, Complete DMEM/F12 media were added instead of virus solution. Drug plating was conducted using a EV0100, 96MAC (Tecan) and virus was added using MicroFlo (Biotek). The assay plates were incubated for five days at 37° C., 5% $CO_2$ and 90% relative humidity.

Endpoint Read: The assay plates were equilibrated to room temperature for 30 minutes and then an equal volume of CellTiter-Glo reagent (Promega Inc.) was added to each well. Plates were incubated for 10 min at room temperature and luminescence was measured using a Synergy4 multi-label reader.

HEp2 Cytotoxicity Assay for VEEV Compounds

Cell Culture: HEp-2 cells (ATCC CCL-23, American Tissue Culture Type) were maintained as adherent cell lines in DMEM with 2 mM L-glutamine and 10% fetal bovine serum (FBS) at 37° C. in a humidified 5% $CO_2$ atmosphere. Cells were passaged as needed and harvested from flasks using 0.05% trypsin-EDTA.

Assay Media—Preparation of Complete DMEM/F12: DMEM/F12 (Invitrogen, Cat. No. 11320) was supplemented with 5 mL of Pen/Strep (Invitrogen, Cat. No. 10378016), 5 mL of 200 mM glutamine (Invitrogen, Cat No. 25030-081), and 10 mL of HI-FBS was added per 500 mL of media.

Dose Response Compound Preparation: For dose response screening, compounds or carrier control (DMSO) were diluted to 3× in Complete DMEM/F12. Test compounds were serially diluted 1:2 resulting in an 8 point dose response dilution series. (final plate well concentration ranging from 50 μM to 0.39 μM and a final DMSO concentration of 0.25%). 30 μL of each dilution was dispensed to assay plates (0.75% DMSO) in triplicate.

Control Drug: The positive control drug for this assay, MPA was solubilized in DMSO.

Preparation of HEp-2 cells: Cells were harvested and resuspended to 267,000 cells per ml in Complete DMEM/F12.

Assay Set up: Forty five ul of HEp-2 cell suspension (12,000 cells/well) were plated in clear bottom black well 96-well plates and the plates were incubated in an incubator at 37° C. in a humidified 5% $CO_2$ atmosphere. The next day, 30 μL of drugging media (0.75% DMSO) were added to the each wells and the plates were incubated at 37° C. for an hour. Each well then received 15 μL of Complete DMEM/F12 media. For the cell control wells, Complete DMEM/F12 media were added instead of virus solution. Drug plating was conducted using a EV0100, 96MAC (Tecan) and virus was added using MicroFlo (Biotek). The assay plates were incubated for five days at 37° C., 5% $CO_2$ and 90% relative humidity.

Endpoint Read: The assay plates were equilibrated to room temperature for 30 minutes and then an equal volume of CellTiter-Glo reagent (Promega Inc.) was added to each well. Plates were incubated for 10 min at room temperature and luminescence was measured using a Synergy4 multi-label reader.

Cell-Based Secondary Assay for Compounds that Inhibit VEEV, TC-83 and Other Alphaviruses (Chikungunya Virus).

Cell Culture: Vero 76 cells obtained from ATCC (CRL-1587) were cultured and maintained in MEM-E (Invitrogen, 10370-088) with 10% Hi-FBS (Invitrogen 16000), 1% Penicillin/Streptomycin/L-glutamine (Invitrogen 10378-024) and 1% HEPES (Invitrogen 15630-080). The cells are maintained at 37° C., 5.0% $CO_2$ to 100% confluence being passaged 1:4 every 3-4 days. For cell plating, cells were detached from flask bottom by using Trypsin-EDTA solution and then re-suspended in a growth media. Cells were passaged no more than ten times after being thawed.

Compound Dosing/Plating: No positive control. The compounds were diluted in complete growth medium to 6× concentrated dosing solution which was dispensed into 96-well black clear-bottom tissue culture treated plates (25 µL volume).

Dose Response Compound Preparation: The compounds were tested in a dose response format using a 1:2 serial dilution with the highest concentrations starting at 100 µM and extending to 0.78 µM over a 8-dose 1:2 serial dilution pattern. DMSO and compounds were diluted in assay media to 4× and 25 µL was dispensed to assay plates. The final DMSO in the assay for all screening concentrations was 0.25%.

Virus Addition: CHIKV stock was diluted in the culture media to 100 TCID50s/25 µL, and 25 µL were added to each test well.

Cell Plating and virus addition: 6,000 cells/well (120,000 cells/ml) were plated in 50 uL using a Matrix WellMate. All additions were done using a Matrix WellMate housed in a class II Biosafety Cabinet within the BSL-2 laboratory. The plates were incubated overnight in an actively humidified incubator with 5.0% $CO_2$ at 37° C. for 18 h and 95% humidity. Compounds (25 µL) were added after the cells had adhered to the plate, and CHIKV virus was added immediately after compound addition. The plates were incubated for 72 h in an actively humidified incubator with 5.0% $CO_2$ at 37° C. for 72 h and 95% humidity, and then endpoint reagent was added.

Endpoint Read: The assay plates were equilibrated to room temperature for 30 minutes and then 100 µL of CellTiter-Glo reagent (Promega Inc.) was added to each well. Plates were incubated for 10 min at room temperature and luminescence was measured using a Perkin Elmer Envision multi-label reader.

Tested Compounds and Results

Testing of Known Compounds for VEEV Inhibitory Activity

A number of compounds were from patent and literature sources with report VEEV inhibitory activity (Scheme 2); however, closer inspection of the data and/or testing in the above-described CPE assay as well as their dependency on host mediated mechanisms of action revealed that the compounds of Scheme 2 suffer from a variety of disadvantages (Table 2).

Scheme 2.

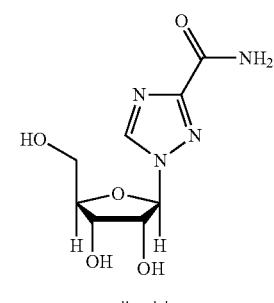

ribavirin

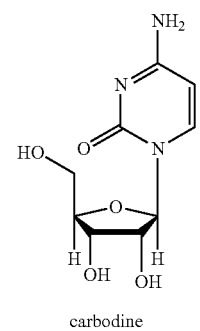

carbodine

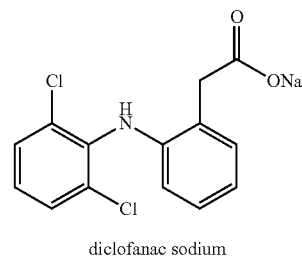

diclofanac sodium

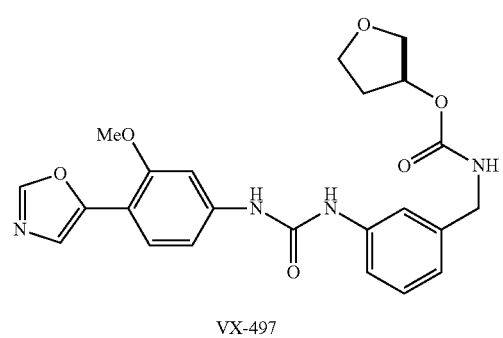

VX-497

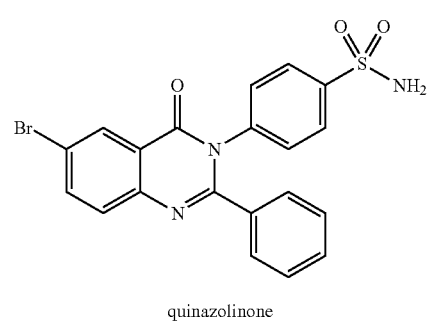

quinazolinone

6 thienylpyrrole

7 antioxidant 80

8 didemnin

TABLE 2

| compound | name | PubChem CID | Reported VEEV CPE inhibition | Assay provided VEEV CPE inhibition | noted liability |
|---|---|---|---|---|---|
| 1 | ribavirin | 37542 | unknown | CPE = 126 µM | not specific to viral target |
| 2 | carbodine | 459903 | unknown | NT | not specific to viral target |
| 3 | diclofenac sodium | 5018304 | unknown | >50 µM | not specific to viral target; NSAID, off target effects |
| 4 | VX-497 | 153241 | CPE = 19.2 µM | NT | not specific to viral target |
| 5 | quinazolinone | 13182904 | CPE = 16.7 µM | CPE >25 µM | mechanism unknown |
| 6 | thienylpyrrole | 3240671 | CPE <100 µM | CPE >25 µM | mechanism unknown |
| 7 | antioxidant 80 | 66662 | unknown | CPE >50 µM | CYP450 (2C9, 2C19) inhibitor ~3 µM |
| 8 | didemnin | 44287859 | unknown | NT | cyclic peptide (non-small molecule) |

In all cases, the reported compounds are either weakly inhibitory against VEEV (>25 µM) and/or do not act selectively on viral components. The interaction of these compounds on cellular components of the host can lead to undesirable toxicity. Ribavirin (Table 2, entry 1) and carbodine (entry 2) are nucleoside anti-metabolite prodrugs with notable clinical toxicities and are not specific in their mechanism of action to viral targets. For example, ribavirin has a broad in vitro inhibitory activity against RNA viruses. The activities include 1) depleting the cellular GTP pool (IMPDH inhibitor), 2) increasing mutations in the viral genome, and 3) inhibiting the GTP capping enzyme. Direct, antiviral activity for ribavirin against Sindbis virus (another alphavirus) has been disclosed, but inhibitory activity for VEEV has not yet been reported. Our testing of ribavirin against VEEV in a CPE assay showed an IC$_{50}$ of 126 μM. Diclofenac (Table 2, entry 3) is a nonsteroidal anti-inflammatory drug (NSAID), thereby acting on cellular components of the host, and was shown to not significantly inhibit VEEV in the CPE assay (>50 μM). Urea VX-497 (Table 2, entry 4) is a potent, reversible uncompetitive IMP dehydrogenase (IMPDH) inhibitor with modest VEEV activity. IMPDH catalyzes an essential step in the de novo biosynthesis of guanine nucleotides, and as such, VX-497 is known to target cellular processes.

The quinazolinone structure (Table 2, entry 5) had a reported VEEV CPE IC$_{50}$ of 16.7 μM. Upon synthesis of the compound for assessment in our internal CPE assay; however, we found the IC$_{50}$ for this compound to be >25 SAR studies provided herein support that quinazolinone should not be active for VEEV.

Thienylpyrrole (Table 2, entry 6) is reported to inhibit WEEV viral replication with an IC$_{50}$=9.3 μM. VEEV inhibition is referred to (<100 μM) for the compound class but is not explicitly reported for any one compound. To dispel ambiguity, the compound was synthesized and assessed in our internal CPE assay, corroborating the finding with a VEEV IC$_{50}$>25 μM.

Antioxidant 80 (Table 2, entry 7) is a broad spectrum antiviral agent due to its antioxidant activity, and it has notable CYP450 (2C9, 2C19) inhibition to the tune of about 3 μM. This compound was purchased and purified prior to submitting to the CPE assay, which resulted in a VEEV IC$_{50}$ of >50 μM.

Lastly, didemnin (Table 2, entry 8) was reported as an active compound for a VEEV screen; however, it is a large cyclic peptide and not an inhibitor of the present technology.

Compounds of Present Technology

Given the modest VEEV inhibition exhibited by the compounds in Table 2, their dependence on host targets, and unclear mechanisms of action, the compounds of the present technology stand out as a first-in-class, potent small molecule VEEV inhibitors. In some embodiments, a potent inhibitor is an inhibitor with a potency <25 μM. In some embodiments, the potency is less than 16 μM. In some embodiments, the potency is a low nanomolar potency. In some embodiments, the compounds exhibit a selectivity index >1500 with respect to cytotoxicity, an ability to reduce viral titer, and a favorable in vitro pharmacokinetic profile which includes moderate blood-brain barrier (BBB) permeability. Without being bound by theory, the compounds of the present technology appear to act through a post-entry, viral-specific, mechanism of action by inhibiting viral replication through the nsP2 helicase. Thus, there are fewer off-target effects because the compounds target the virus and not host.

The following compounds of the present technology were synthesized according the above procedures or slight modifications thereof and were characterized by mass spectroscopy. Each compound gave the expected $^1$H and $^{13}$C NMR spectra, and gave the expected (M+H)$^+$ peaks in the mass spectrum.

Surprisingly, it was discovered that inclusion of an electron withdrawing group at the C6 position of the molecule conferred significant CPE potency. Migration of the nitro group from the C6 position to the C5-, C7- or C8-positions afforded analogs without significant CPE potency (>25 μM, Table 3).

TABLE 3

| Entry | R$_3$ | VEEV CPE Assay Potency mean (μM) (n = # replicates) | | VEEV Cytotoxicity (μM) (n = # replicates) | | Selectivity | VEEV titer reduction mean (log) | |
|---|---|---|---|---|---|---|---|---|
| | | n | IC$_{50}$ μM | n | CC$_{50}$ μM | (CC$_{50}$/IC$_{50}$) | n | log |
| 1 | 6-NO$_2$ | 33 | 0.78 | 7 | >50 | >63.3 | 2 | 6.36 |
| 2 | 7-NO$_2$ | 3 | >25.00 | 1 | >25.00 | 1.00 | 0 | NT |
| 3 | 8-NO$_2$ | 3 | >25.00 | 1 | >25.00 | 1.00 | 0 | NT |
| 4 | 5-NO$_2$ | 3 | >25.00 | 1 | >25.00 | 1.00 | 0 | NT |

NT = not tested.

Substitution of the nitro group was pursued for a select series (Table 4), where inclusion of a nitrile group (entry 6) provided an active compound. A fluorine atom in place of the nitro group was investigated in tandem with other changes (Table 7, entry 8), providing an analog that retained CPE potency. Select compounds from this set were evaluated in a VEEV titer reduction assay. Importantly, for the compounds tested, a strong correlation was found between the CPE and titer reduction assays. A weakly potent compound in the CPE assay translated to a weakly efficacious reduction in viral titer (Table 4, entry 5), while potent compounds produced a robust effect in reducing viral titer (Table 4, entries 1 and 4). Surprisingly, all compounds were nontoxic (CC$_{50}$>25 μM).

TABLE 4

[Structure: quinazolin-4(3H)-one with R1 at 6-position, R2 on N3, and 2-(4-ethylpiperazin-1-ylmethyl) substituent]

| Entry | R₁ | R₂ | n | IC₅₀ μM | n | CC₅₀ μM | Selectivity (CC₅₀/IC₅₀) | n | log |
|---|---|---|---|---|---|---|---|---|---|
| 1 | NO₂ | 2-F-phenyl | 33 | 0.78 | 7 | >50.00 | >63.30 | 2 | 6.36 |
| 2 | H | 2-F-phenyl | 3 | >25.00 | 1 | >25.00 | 1.00 | 0 | NT |
| 3 | CF₃ | 2-F-phenyl | 3 | >25.00 | 1 | >25.00 | 1.00 | 0 | NT |
| 4 | NO₂ | phenyl | 18 | 0.25 | 1 | >25.00 | 1.00 | 4 | >7.76 |
| 5 | I | phenyl | 3 | 17.06 | 1 | >25.00 | >1.50 | 2 | 0.33 |
| 6 | CN | phenyl | 3 | 1.14 | 1 | >25.00 | >21.90 | 0 | NT |
| 7 | SOH | phenyl | 3 | >25.00 | 1 | >25.00 | 1.00 | 0 | NT |
| 8 | CO₂H | phenyl | 3 | >25.00 | 1 | >25.00 | 1.00 | 0 | NT |
| 9 | NH-tetrazole | phenyl | 3 | >50.00 | 1 | >50.00 | 1.00 | 0 | NT |
| 10 | CONH₂ | phenyl | 3 | >25.00 | 1 | >25.00 | 1.00 | 0 | NT |
| 11 | CONMe₂ | phenyl | 3 | >25.00 | 1 | >25.00 | 1.00 | 0 | NT |
| 12 | 2-pyridyl | phenyl | 3 | >50.00 | 1 | >50.00 | 1.00 | 0 | NT |
| 13 | 3-pyridyl | phenyl | 3 | >25.00 | 1 | >25.00 | 1.00 | 0 | NT |

Column headers (full): VEEV TC-83 CPE assay potency mean (μM) (n = # replicates); VEEV cytotoxicity assay (mean (μM)) (n = # replicates); Selectivity; VEEV TC-83 titer reduction mean (log).

NT = not tested.

A few other changes involving the fused phenyl ring of the quinazolinone core included replacement of the C8 CH-atoms with a nitrogen atom or 6,7-difluorosubstitution (Scheme 3). Incorporation of the nitrogen atom did not significantly alter the CPE potency profile from that the carbon analog at position 8 (Table 4, entry 4). Difluorosubstitution retained CPE activity.

Scheme 3.

[Structure: 6-nitro-pyrido[2,3-d]pyrimidin-4(3H)-one analog with N-phenyl and 2-(4-ethylpiperazin-1-ylmethyl)]

CPE EC₅₀ = 0.83 μM
CC₅₀ > 25 μM

[Structure: 6,7-difluoro-3-phenylquinazolin-4(3H)-one with 2-(piperazin-1-ylmethyl)]

CPE EC₅₀ = 22.5 μM
CC₅₀ > 50 μM

Given the potency afforded by the inclusion of the C6 nitro functionality, a SAR was investigated with this moiety preserved (Table 5). Attention shifted to derivitization of the 2-fluorophenyl amide substituent. The N-ethyl piperazine was initially used until it was determined that the N—H piperazine comparatively offered a slightly improved CPE potency while reducing molecular weight and adjusting c Log P (Table 5, entries 4 vs 9).

TABLE 5

[Structure: 6-nitroquinazolin-4(3H)-one with R2 on N3 and 2-((4-R3-piperazin-1-yl)methyl) substituent]

| Entry | R₂ | R₃ | n | IC₅₀ μM | n | CC₅₀ μM | Selectivity (CC₅₀/IC₅₀) | n | log |
|---|---|---|---|---|---|---|---|---|---|
| 1 | 2-F-phenyl | ethyl | 33 | 0.78 | 7 | >50.00 | >63.3 | 2 | 6.36 |
| 2 | 3-F-phenyl | ethyl | 6 | 0.38 | 2 | >25.00 | >65.79 | 4 | 7.11 |
| 3 | 4-F-phenyl | ethyl | 6 | 0.80 | 2 | >25.00 | >31.25 | 4 | 5.88 |
| 4 | phenyl | ethyl | 9 | 0.22 | 2 | >25.00 | >113.64 | 4 | >7.76 |
| 5 | methyl | ethyl | 3 | >25.00 | 1 | >25.00 | 1.00 | 0 | NT |
| 6 | i-propyl | ethyl | 3 | >25.00 | 1 | >25.00 | 1.00 | 0 | NT |
| 7 | benzyl | ethyl | 3 | >25.00 | 1 | >25.00 | 1.00 | 0 | NT |
| 8 | H | ethyl | 3 | >25.00 | 1 | >25.00 | 1.00 | 0 | NT |
| 9 | phenyl | H | 3 | 0.15 | 1 | >25.00 | >166.67 | 2 | >7.76 |

Column headers (full): VEEV CPE Assay Potency mean (μM) (n = # replicates); VEEV Cytotoxicity Assay mean (μM) (n = # replicates); Selectivity; VEEV titer reduction assay mean (log).

TABLE 5-continued

| | | | VEEV CPE Assay Potency mean (μM) (n = # replicates) | | VEEV Cytotoxicity Assay mean (μM) (n = # replicates) | | Selectivity | VEEV titer reduction assay mean (log) | |
|---|---|---|---|---|---|---|---|---|---|
| Entry | R$_2$ | R$_3$ | n | IC$_{50}$ μM | n | CC$_{50}$ μM | (CC$_{50}$/IC$_{50}$) | n | log |
| 10 | 2-MeO-phenyl | H | 3 | >25.00 | 1 | >25.00 | 1.00 | 0 | NT |
| 11 | 3-MeO-phenyl | H | 3 | 5.13 | 1 | >25.00 | 4.87 | 0 | NT |
| 12 | 4-MeO-phenyl | H | 6 | 0.24 | 2 | >25.00 | >104.17 | 0 | NT |
| 13 | 3-NMe$_2$-phenyl | H | 3 | >25.00 | 1 | >25.00 | 1.00 | 0 | NT |
| 14 | 4-NMe$_2$-phenyl | H | 3 | >25.00 | 1 | >25.00 | 1.00 | 0 | NT |
| 15 | 3-thiophene | H | 3 | 1.36 | 1 | >25.00 | >18.38 | 0 | NT |

NT = not tested.

Compared to the 2-fluorophenyl group (Table 5, entry 1), a two-fold improvement in CPE potency and almost one log increase in titer reduction was observed by switching to the 3-fluorophenyl group (entry 2); however, removal of the fluorine atom further provided slight improvements in both assays (entry 4) such that the titer reduction assay pegged at the maximum of >7.76 log. As noted previously, the N—H piperazine afforded a boost in CPE potency (entry 9) and also pegged the assay for reduction in viral titer.

Modifications to the piperazine moiety were also tested (Table 6). Replacement of the ethyl group for methyl was inconsequential, but an isopropyl group notably attenuated activity (entry 3, Table 6). Without being bound by theory, the differing activity due to the alkyl group at this position suggests a spacial constraint in the binding site.

An N-phenyl group (Table 6, entry 4) reduced activity. Without being bound by theory, this may be due to steric factors or due to the preference of a basic amine that makes beneficial interations with proximal residues in the binding site. The N—H analog was superior to all others in this set (Table 6, entry 5) for both CPE potency and reduction in viral titer. The non-basic, but still sterically-demanding N—BOC analog was inactive. Replacement of the amine with an oxygen atom or methylene unit provided activity, albeit reduced, in both CPE and titer reduction assays (Table 6, entries 7-8, respectively). The NH amide (Table 6, entry 9) was prepared as a less spacially consuming, non-basic, NH-moiety and was determined to be inactive. Notably, the titer reduction data was negatively impacted significantly, underscoring the tracking between the CPE and titer reduc-

TABLE 6

| | | | TC-83 VEEV CPE Assay Potency mean (μM) (n = # replicates) | | Cytotoxicity Assay mean (μM) (n = # replicates) | | Selectivity | TC-83 VEEV titer reduction assay mean (log) (n = # replicates) | |
|---|---|---|---|---|---|---|---|---|---|
| Entry | X | R$_3$ | n | IC$_{50}$ μM | n | CC$_{50}$ μM | (CC$_{50}$/IC$_{50}$) | n | log |
| 1 | CH$_2$ | N-ethyl | 33 | 0.78 | 7 | >50.00 | >63.30 | 2 | 6.36 |
| 2 | CH$_2$ | N-methyl | 9 | 0.79 | 3 | >50.00 | >63.30 | 4 | 7.08 |
| 3 | CH$_2$ | N-i-propyl | 3 | 4.42 | 1 | >50.00 | >11.31 | 0 | NT |
| 4 | CH$_2$ | N-phenyl | 3 | >50.00 | 1 | >50.00 | 1.00 | 0 | NT |
| 5 | CH$_2$ | N—H | 6 | 0.24 | 2 | >25.00 | >104.17 | 4 | >7.76 |
| 6 | CH$_2$ | N—BOC | 3 | >25.00 | 1 | >25.00 | 1.00 | 0 | NT |
| 7 | CH$_2$ | O | 3 | 8.67 | 1 | >50.00 | >5.77 | 2 | 0.3 |
| 8 | CH$_2$ | CH$_2$ | 3 | 4.70 | 1 | >25.00 | >5.32 | 2 | 0.37 |
| 9 | CO | NH | 3 | >50.00 | 1 | >50.00 | 1.00 | 0 | NT |

NT = not tested.

tion assays. Without being bound by theory, these combined results suggested (but do not completely clarify) a preference for a basic NH moiety in this region of the compound. Surprisingly, all compounds in this set were nontoxic (>25 µM).

More extensive modifications were made to the alkylpiperazine appendage to gauge the need for the methylene linkage between the quinazolinone core and piperazine group (Scheme 4). Excision of the methylene linkage and direct attachment of the piperazine to the core resulted in an inactive analog. Concomitant methylene linkage removal with nitrogen replacement by CH provided CPE activity (3.57 µM). Reduction of the imine core was not tolerated.

Scheme 4.

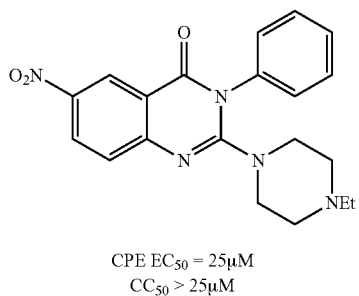

CPE EC$_{50}$ = 25µM
CC$_{50}$ > 25µM

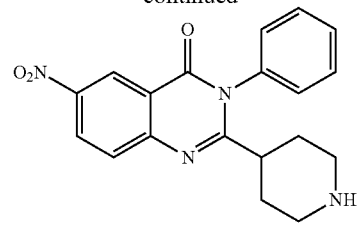

CPE EC$_{50}$ = 3.57µM
CC$_{50}$ > 25µM

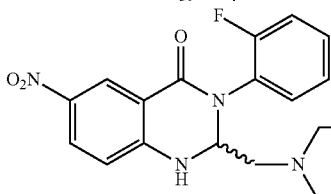

CPE EC$_{50}$ = 25µM
CC$_{50}$ > 25µM

Alterations in the piperazine moiety were also studied (Table 7). Migration of the NH component over one methylene unit to provide a hexahydropyrimidine (Table 7, entry 2) or ring expansion to the 1,4-diazepane (Table 7, entry 3) yielded compounds that possessed respectable CPE activity. Ring opened varieties were also investigated. A dialkyldiamine bearing a three-carbon linker showed slightly improved potency (Table 7, entry 4).

TABLE 7

| | | | | TC-83 VEEV CPE Assay Potency mean (µM) (n = # replicates) | | Cytotoxicity Assay mean (µM) (n = # replicates) | | Selectivity | TC-83 VEEV titer reduction assay mean (log) | |
|---|---|---|---|---|---|---|---|---|---|---|
| Entry | R$_1$ | R$_2$ | R$_3$ | n | IC$_{50}$ µM | n | CC$_{50}$ µM | (CC$_{50}$/IC$_{50}$) | n | log |
| 1 | NO$_2$ | 2-F-phenyl | | 33 | 0.78 | 7 | >50.00 | >63.3 | 2 | 6.36 |
| 2 | NO$_2$ | phenyl | | 3 | 1.13 | 1 | >50.00 | >44.2 | 0 | NT |
| 3 | NO$_2$ | phenyl | | 3 | 0.94 | 1 | >50.00 | >53.2 | 0 | NT |
| 4 | NO$_2$ | phenyl | | 3 | 0.61 | 1 | >50.00 | >82.0 | 0 | NT |

NT = not tested

However, the greatest improvement was observed with the amidines formed from ring opening of the quinazolinone (Table 8, entries 1-2). These changes afforded compounds with at least a 15-fold gain in CPE potency over entry 1 of Table 7. Given the significant progress made at this point, other permissible or advantageous substitutions in other regions of the scaffold were incorporated to survey effects on potency, c Log P, stability, solubility, and BBB permeability in an effort to tune and maximize the desired profile of the potential probe. Replacement of the nitro group with either a nitrile (Table 8, entry 3) or a fluorine atom (Table 8, entry 4) did not extinguish potency; however, installation of the 4-methoxyphenyl substitutent at $R_2$ generated another valuable and potent analog (Table 7, entry 5).

TABLE 8

| Entry | $R_1$ | $R_2$ | $R_3$ | n | TC-83 VEEV CPE Assay Potency mean ($\mu$M) IC$_{50}$ $\mu$M | n | Cytotoxicity Assay mean ($\mu$M) CC$_{50}$ $\mu$M | Selectivity (CC$_{50}$/IC$_{50}$) | n | TC-83 VEEV titer reduction assay mean (log) |

TABLE 8-continued

Structure: R1-substituted benzamide with NHR2 and N=R3 (hydrazone), where R3 is 1,4-dimethylpiperazin-2-ylidene.

| Entry | R1 | R2 | R3 | n | IC50 μM | n | CC50 μM | Selectivity (CC50/IC50) | n | log |
|---|---|---|---|---|---|---|---|---|---|---|
| 7 | NC | 3-F-phenyl | 1,4-dimethylpiperazin-2-ylidene | 3 | 0.84 | 2 | >50.00 | >59.5 | 0 | NT |

NT = not tested

Further substitutions made towards assessing the potency of analogs are provided in Table 9.

TABLE 9

Structure: R1, X-substituted benzamide with NHR2 and N=R3 (hydrazone), R3 = 1,4-dimethylpiperazin-2-ylidene.

| Entry | R1 | R2 | R3 | X | IC50 μM |
|---|---|---|---|---|---|
| 1 | CN | phenyl | 1,4-dimethylpiperazin-2-ylidene | Cl | 0.13 |
| 2 | CN | 2-F-phenyl | 1,4-dimethylpiperazin-2-ylidene | H | 3.69 |
| 3 | NO2 | 3-F-phenyl | 1,4-dimethylpiperazin-2-ylidene | H | 0.1 |
| 4 | NO2 | 4-F-phenyl | 1,4-dimethylpiperazin-2-ylidene | H | 0.09 |
| 5 | NO2 | benzyl | 1,4-dimethylpiperazin-2-ylidene | H | 3.65 |
| 6 | MeO(O)C— | phenyl | 1,4-dimethylpiperazin-2-ylidene | H | 1.98 |
| 7 | NO2 | thiophen-3-yl-methyl | 1,4-dimethylpiperazin-2-ylidene | H | 0.54 |

TABLE 9-continued

| Entry | R1 | R2 | R3 | X | TC-83 VEEV CPE Assay Potency mean (μM) IC50 μM |
|---|---|---|---|---|---|
| 8 | F | phenyl | 2-(1,4-dimethylpiperazin-2-ylidene) | F | 4.4 |
| 9 | CN | phenyl | 2-(1,4-dimethylpiperazin-2-ylidene) | F | 0.43 |
| 10 | CF3 | phenyl | 2-(1,4-dimethylpiperazin-2-ylidene) | H | 22.3 |
| 11 | NO2 | 3-MeO-phenyl | 2-(1,4-dimethylpiperazin-2-ylidene) | H | 8.07 |
| 12 | NO2 | (CH3)2CH— | 2-(1,4-dimethylpiperazin-2-ylidene) | H | 27 |
| 13 | H | phenyl | 2-(1,4-dimethylpiperazin-2-ylidene) | F | >300 |
| 14 | NO2 | 2-MeO-phenyl | 2-(1,4-dimethylpiperazin-2-ylidene) |  | 33.7 |

In addition, 2-((1-methylpiperidin-4-yl)amino)-5-nitro-N-phenylbenzamide was synthesized to assess the influence of the amidine ring on the potency.

2-((1-methylpiperidin-4-yl)amino)-5-nitro-N-phenyl-benzamide

It was found that this variant exhibited a potency of 41.2 μM in the TC-83 VEEV CPE assay. Thus, structural modification of this type eroded potency against VEEV.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound of Formula I:

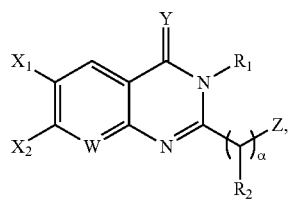

stereoisomers thereof and pharmaceutically acceptable salts thereof, wherein:

W is CH or N;
$X_1$ is a halogen, a nitro group, cyano group, an alkanoyl group, a carbamoyl group, an ester, a sulfonyl group, a trialkyl ammonium group, or a trifluoromethyl group;
$X_2$ is hydrogen, a halogen, a nitro group, or a cyano group;
Y is O or S;
$R_1$ is thiophen-3-yl or a phenyl group, wherein the phenyl group is of Formula IA:

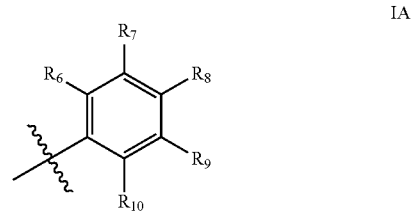

where $R_6$ $R_7$, $R_8$, $R_9$ and $R_{10}$ are each independently hydrogen, halo, alkoxy, alkanoyl, carbamoyl, cyano, trifluoromethyl, or nitro;
$R_2$ is hydrogen;
$R_3$ is hydrogen or alkyl;
$R_4$ is hydrogen or alkyl;
α is 0 or 1;
B is CH, C-alkyl, O, or N; with the provision that when B is O, $R_4$ is absent;
Z is selected from the group consisting of

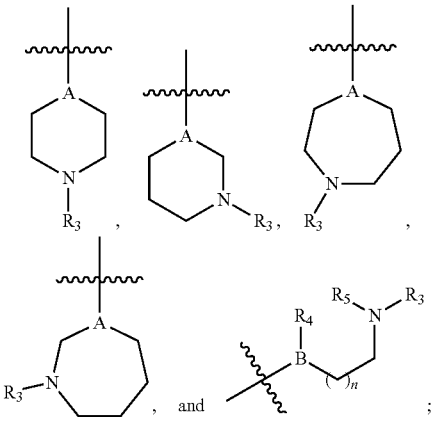

where $R_5$ is hydrogen or alkyl;
A is CH, C-alkyl, or N; and
n is 1, 2, 3, or 4.

2. The compound of claim 1, wherein $X_2$ is hydrogen.

3. The compound of claim 1, wherein
Y is O,
α is 1; and
n is 1, 2, or 3.

4. The compound of claim 1, wherein
$X_1$ is a halogen, a nitro group, or cyano group;
$X_2$ is hydrogen;
Y is O;
α is 1;
B is CH, C-alkyl, or N; and
n is 2 or 3.

5. The compound of claim 1, wherein $R_6$ is hydrogen.

6. The compound of claim 1, wherein Z is

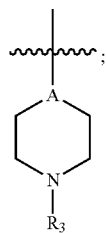

and R₃ is hydrogen.

7. The compound of claim 1, wherein W is CH.

8. The compound of claim 1, wherein $R_1$ is a phenyl group of Formula IA:

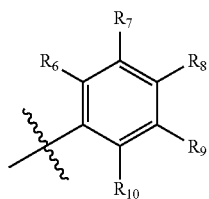

where $R_6$ is hydrogen;
$R_7$, and $R_8$ are each independently hydrogen, methoxy, or halo;
$R_9$ and $R_{10}$ are each independently hydrogen.

9. The compound of claim 4, wherein Z is

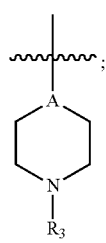

and $R_3$ is hydrogen.

10. The compound of claim 4, wherein W is CH.

11. The compound of claim 4, wherein $R_1$ is a phenyl group of Formula IA:

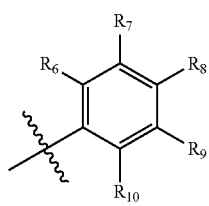

where $R_6$ is hydrogen;
$R_7$, and $R_8$ are each independently hydrogen, methoxy, or halo;
$R_9$ and $R_{10}$ are each independently hydrogen.

12. The compound of claim 1, wherein the compound is selected from the group consisting of 2-((4-ethylpiperazin-1-yl)methyl)-6-nitro-3-phenylquinazolin-4(3H)-one, 6-nitro-3-phenyl-2-(piperazin-1-ylmethyl)quinazolin-4(3H)-one, 6-nitro-2-(piperazin-1-ylmethyl)-3-(thiophen-3-yl)quinazolin-4(3H)-one, 3-(2-fluorophenyl)-2-((4-methylpiperazin-1-yl)methyl)-6-nitroquinazolin-4(3H)-one, 2-((4-ethylpiperazin-1-yl)methyl)-3-(2-fluorophenyl)-6-nitroquinazolin-4(3H)-one, 2-((4-ethylpiperazin-1-yl)methyl)-3-(3-fluorophenyl)-6-nitroquinazolin-4(3H)-one, 24(4-ethylpiperazin-1-yl)methyl)-3-(4-fluorophenyl)-6-nitroquinazolin-4(3H)-one, 3-(2-fluorophenyl)-2-((4-isopropylpiperazin-1-yl)methyl)-6-nitroquinazolin-4(3H)-one, 3-(2-fluorophenyl)-6-nitro-2-(piperazin-1-ylmethyl)quinazolin-4(3H)-one, 3-(2-fluorophenyl)-2-(morpholinomethyl)-6-nitroquinazolin-4(3H)-one, 3-(2-fluorophenyl)-6-nitro-2-(piperidin-1-ylmethyl)quinazolin-4(3H)-one, 3-(3-methoxyphenyl)-6-nitro-2-(piperazin-1-ylmethyl)quinazolin-4(3H)-one, 3-(4-methoxyphenyl)-6-nitro-2-(piperazin-1-ylmethyl)quinazolin-4(3H)-one, 2-((4-ethylpiperazin-1-yl)methyl)-6-iodo-3-phenylquinazolin-4(3H)-one, 2-((4-ethylpiperazin-1-yl)methyl)-4-oxo-3-phenyl-3,4-dihydroquinazoline-6-carbonitrile, 6-nitro-3-phenyl-2-((tetrahydropyrimidin-1(2H)-yl)methyl)quinazolin-4(3H)-one, 2-((1,4-diazepan-1-yl)methyl)-6-nitro-3-phenylquinazolin-4(3H)-one, 2-((methyl(2-(methylamino)ethyl)amino)methyl)-6-nitro-3-phenylquinazolin-4(3H)-one, 2-((methyl(3-(methylamino)propyl)amino)methyl)-6-nitro-3-phenylquinazolin-4(3H)-one, 2-(((2-(ethylamino)ethyl)(methyl)amino)methyl)-6-nitro-3-phenylquinazolin-4(3H)-one, 3-(4-methoxyphenyl)-2-((methyl(2-(methylamino)ethyl)amino)methyl)-6-nitroquinazolin-4(3H)-one, 3-(2-fluorophenyl)-2-((methyl(2-(methylamino)ethyl)amino)methyl)-6-nitroquinazolin-4(3H)-one, 3-(3-fluorophenyl)-2-((methyl(2-(methylamino)ethyl)amino)methyl)-4-oxo-3,4-dihydroquinazoline-6-carbonitrile, 6-fluoro-2-((methyl(2-(methylamino)ethyl)amino)methyl)-3-phenylquinazolin-4(3H)-one, 2-((methyl(2-(methylamino)ethyl)amino)methyl)-4-oxo-3-phenyl-3,4-dihydroquinazoline-6-carbonitrile, 2-((4-ethylpiperazin-1-yl)methyl)-6-nitro-3-phenylpyrido[2,3-d]pyrimidin-4(3H)-one, and 6-nitro-3-phenyl-2-(piperidin-4-yl)quinazolin-4(3H)-one.

13. A composition comprising a compound of claim 1 and a pharmaceutically acceptable carrier.

14. The compound of claim 3, wherein Z is selected from the group consisting of
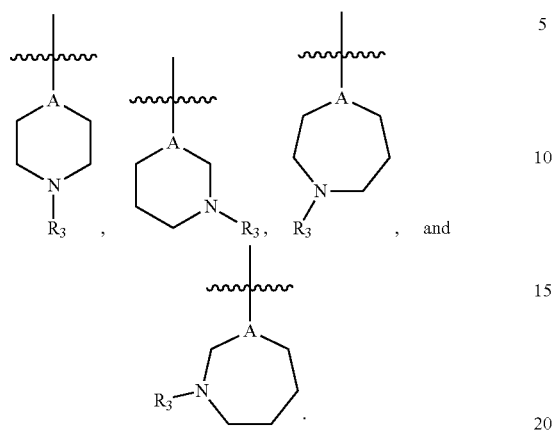
15. A composition comprising a compound of claim 14 and a pharmaceutically acceptable carrier.
16. A composition comprising a compound of claim 9 and a pharmaceutically acceptable carrier.
* * * * *